(12) United States Patent
Kamon

(10) Patent No.: US 11,200,460 B2
(45) Date of Patent: Dec. 14, 2021

(54) IMAGE LEARNING DEVICE, IMAGE LEARNING METHOD, NEURAL NETWORK, AND IMAGE CLASSIFICATION DEVICE

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/089,673

(22) Filed: Nov. 4, 2020

(65) Prior Publication Data

US 2021/0158100 A1    May 27, 2021

(30) Foreign Application Priority Data

Nov. 27, 2019    (JP) .............................. JP2019-214139

(51) Int. Cl.
| | |
|---|---|
| *G06K 9/62* | (2006.01) |
| *G06N 3/08* | (2006.01) |
| *G16H 30/20* | (2018.01) |
| *G16H 30/40* | (2018.01) |

(52) U.S. Cl.
CPC ......... *G06K 9/6259* (2013.01); *G06K 9/6267* (2013.01); *G06N 3/08* (2013.01); *G16H 30/20* (2018.01); *G16H 30/40* (2018.01)

(58) Field of Classification Search
CPC ...... G06K 9/6259; G06K 9/6267; G06N 3/08; G16H 30/20; G16H 30/40; G16H 40/63; G16H 50/20; G16H 50/30; G16H 50/70
See application file for complete search history.

(56) References Cited

U.S. PATENT DOCUMENTS

| 9,911,067 B2 | 3/2018 | Hikida | |
|---|---|---|---|
| 10,387,753 B1 * | 8/2019 | Kim | ..................... G06K 9/3233 |
| 2018/0293496 A1 * | 10/2018 | Vogels | ..................... G06N 3/084 |
| 2020/0005098 A1 * | 1/2020 | Sung | ........................ G06K 9/66 |
| 2020/0374600 A1 * | 11/2020 | Xu | .................... H04N 21/44008 |
| 2021/0133474 A1 * | 5/2021 | Sawada | ..................... G06T 7/73 |

FOREIGN PATENT DOCUMENTS

JP         2016033806         3/2016

* cited by examiner

*Primary Examiner* — Xin Jia
(74) *Attorney, Agent, or Firm* — JCIPRNET

(57) ABSTRACT

An object of the invention is to provide an image learning device, an image learning method, a neural network, and an image classification device which can support appropriate classification of an image.
In the image learning device according to an aspect of the invention, the neural network performs a first task of classifying a recognition target in a medical image and outputting a classification score as an evaluation result, and a second task different from the first task. The neural network updates a weight coefficient on the basis of a comparison result between the classification score output for the medical image of a first image group and a ground truth classification label, and does not reflect the classification score output for the medical image of a second image group in an update of the weight coefficient, for the first task. The neural network updates the weight coefficient on the basis of the evaluation result output for the medical image of the first image group and the evaluation result output for the medical image of the second image group, for the second task.

13 Claims, 20 Drawing Sheets

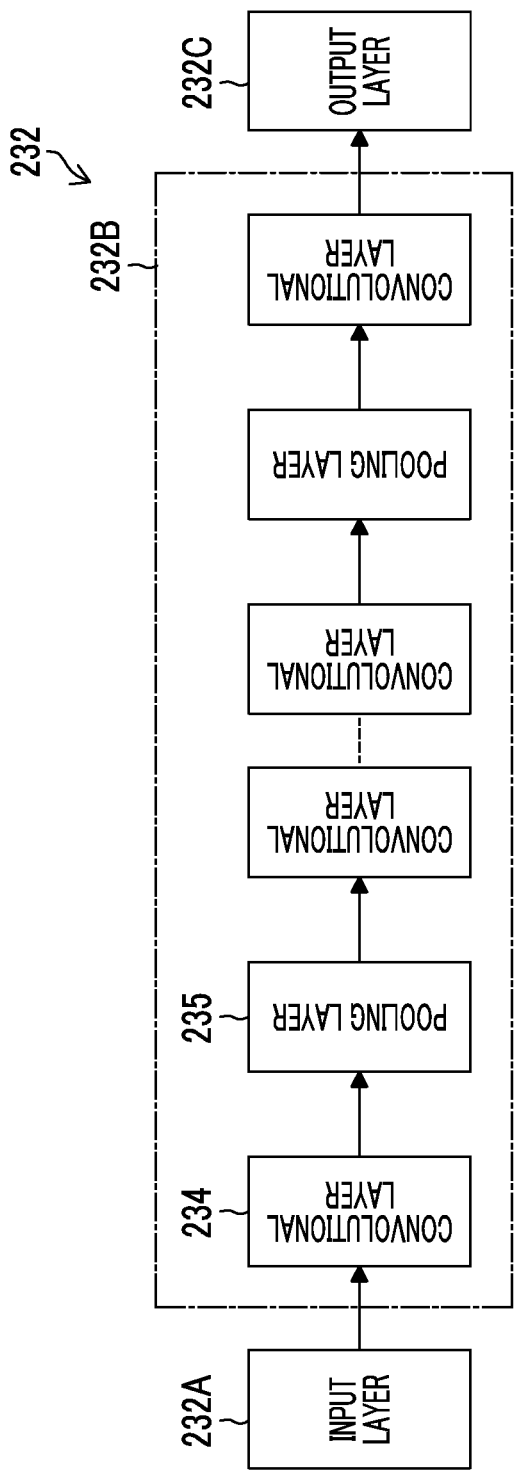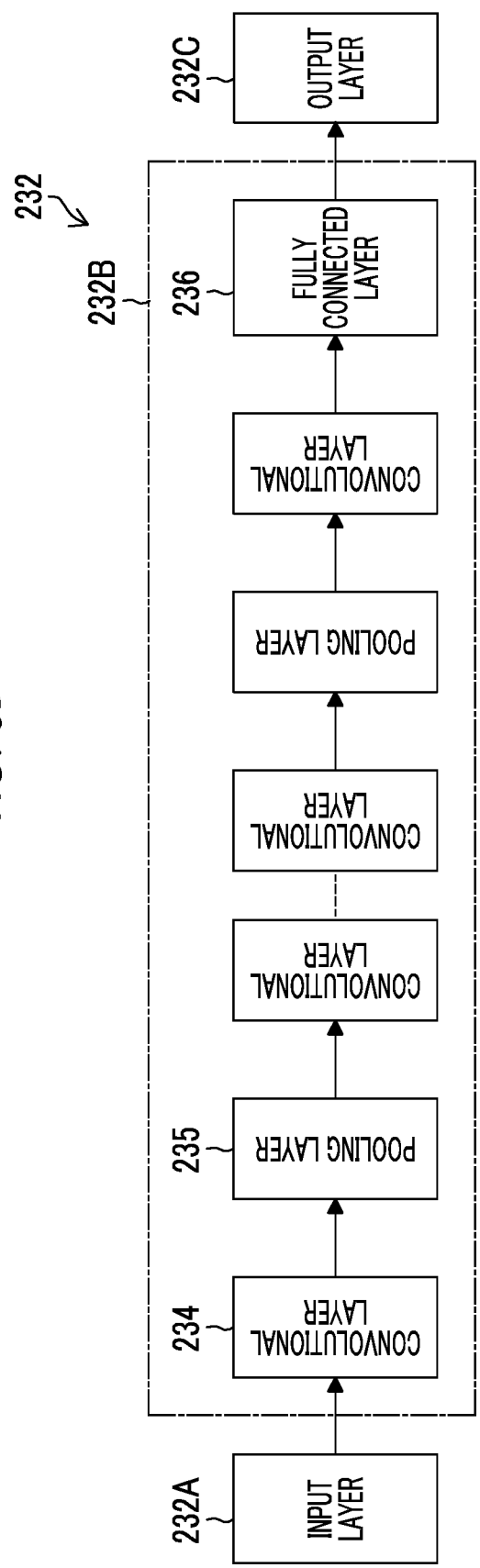

IMAGE LEARNING DEVICE, IMAGE LEARNING METHOD, NEURAL NETWORK, AND IMAGE CLASSIFICATION DEVICE

CROSS-REFERENCE TO RELATED APPLICATIONS

The present application claims priority under 35 U.S.C § 119 to Japanese Patent Application No. 2019-214139 filed on Nov. 27, 2019. The above application is hereby expressly incorporated by reference, in its entirety, into the present application.

BACKGROUND OF THE INVENTION

1. Field of the Invention

The present invention relates to an image learning device, an image learning method, a neural network, and an image classification device which recognize an image.

2. Description of the Related Art

There has been known a technique of performing image recognition (for example, classification) using a recognizer configured by machine learning. In such a technique, learning is performed by, for example, giving learning data to a neural network and performing error backpropagation on the basis of a recognition result (classification result or the like). Such a technique is disclosed in JP2016-033806A, for example.

SUMMARY OF THE INVENTION

In a case where images are automatically classified by a recognizer configured by machine learning, an incorrect result may be output in response to a structure other than a classification target. For example, in a case where the benignancy or malignancy of a lesion in a medical image is automatically classified, the recognizer may erroneously determine the residue, instead of the lesion, in the image as a malignant lesion to output an incorrect classification result. However, the technique in the related art as disclosed in JP2016-033806A has not been able to deal with such a problem.

The invention has been made in view of such circumstances, and an object of the invention is to provide an image learning device, an image learning method, a neural network, and an image classification device which can support appropriate classification of images.

An image learning device according to a first aspect of the invention comprises a first image acquisition unit that acquires a first image group composed of images each including at least one recognition target; a second image acquisition unit that acquires a second image group composed of images not including the recognition target; a ground truth data acquisition unit that acquires ground truth data associated with the images; and a neural network that includes an input unit that inputs an image, a weight coefficient storage unit that stores a weight coefficient to be applied to the input image, and an output unit that outputs an evaluation result of the input image on the basis of the input image and the weight coefficient, and performs a first task of classifying the recognition target in the input image and outputting a classification score as the evaluation result, and a second task which is different from the first task and is performed on the input image, in which the ground truth data acquisition unit acquires a ground truth classification label associated with the image of the first image group as the ground truth data, for the first task, and acquires the ground truth data associated with the image of the first image group and the ground truth data associated with the image of the second image group, for the second task, and the neural network, for the first task, updates the weight coefficient on the basis of a comparison result between the classification score output for the image of the first image group and the ground truth classification label, and does not reflect the classification score output for the image of the second image group in an update of the weight coefficient, and for the second task, updates the weight coefficient on the basis of the evaluation result output for the image of the first image group and the evaluation result output for the image of the second image group.

In a case of the learning of a convolutional neural network (CNN), label information as the ground truth class of the recognition target is given to an image including the recognition target (object), and the weight coefficient of the CNN is updated such that the output of the CNN in a case where the image is input approaches the label. Accordingly, it is possible to infer the class of the recognition target for the image including the recognition target.

However, in actual operation, the input image does not always include the recognition target. For example, in some cases, an image not including a lesion is input to the CNN that classifies the type of lesions. In such a case, an incorrect result may be output as the classification result although the recognition target is not included. Therefore, by adding such images not including the recognition target to the learning data, it is necessary to perform learning such that the output is controlled by any method.

Here, in a case where the image not including the recognition target is added to the learning data, handling the classification problems in the learning part becomes a problem. Since the added data does not include the recognition target, that is, a predetermined class is not present, label information cannot be given. Classification can be learned by expanding the predetermined class ("others" class is added to the existing classification of N classes to make classification of N+1 classes), but there is a problem in that the model becomes complicated because the number of classification classes is increased.

In view of such circumstances, in the image learning device according to the first aspect, for the first task (classification), the weight coefficient is updated on the basis of the comparison result between the classification score output for the image of the first image group and the ground truth classification label, and the classification score output for the image of the second image group is not reflected in the update of the weight coefficient. On the other hand, for the second task, the weight coefficient is updated on the basis of the evaluation result output for the image of the first image group and the evaluation result output for the image of the second image group. Accordingly, it is possible to add images not including the recognition target to the learning data without the model being complicated, and to support appropriate classification of images.

As a method of controlling the update of the weight coefficient, a method of "performing control such that the value of a loss function calculated from the score becomes zero" or "performing control such that the gradient of a loss function during error backpropagation becomes zero" is exemplified.

In the first aspect, the image learning device according to a second aspect further comprises a region information acquisition unit that acquires region information of the recognition target in the image, for at least one image of the first image group, in which the ground truth data acquisition unit further includes a segmentation label generation unit that generates, as the ground truth data, a ground truth segmentation label associated with the image, for the image, for which the region information is acquired, among the images of the first image group and the image of the second image group, assigns a predetermined class as the ground truth segmentation label, for all of small regions of the image of the second image group and a small region not corresponding to the recognition target among small regions of the image of the first image group, and assigns a class label different from the predetermined class, as the ground truth segmentation label, for a small region corresponding to the recognition target among the small regions of the image of the first image group, and the neural network has a segmentation score output unit that performs segmentation as the second task on the basis of the image input by the input unit and the weight coefficient, and outputs a segmentation score as the evaluation result for each small region of the image, and the neural network updates the weight coefficient on the basis of a comparison result between the segmentation score output by inputting the image of the first image group and the image of the second image group and the ground truth segmentation label associated with the input image. In the second aspect, "predetermined class" may be a "background class" indicating a region which does not include a target of the first task (classification).

In the second aspect, in the image learning device according to a third aspect, the neural network does not reflect the segmentation score output for the image, for which the region information is not acquired, among the images of the first image group in the update of the weight coefficient.

In the second or third aspect, in the image learning device according to a fourth aspect, the ground truth segmentation label has a lower resolution than a resolution of the input image.

In the first aspect, the image learning device according to a fifth aspect further comprises a positional information acquisition unit that acquires positional information of the recognition target in the image, for at least one image of the first image group, in which the ground truth data acquisition unit further includes a ground truth position label generation unit that generates, as the ground truth data, a ground truth position label associated with the image, for the image, for which the positional information is acquired, among the images of the first image group and the image of the second image group, assigns a ground truth position label indicating that the recognition target is not present to the image of the second image group, and assigns a ground truth position label corresponding to a position of the recognition target to the image of the first image group, the neural network has an estimated positional information output unit that estimates positional information of the recognition target as the second task and outputs estimated positional information as the evaluation result on the basis of the image input by the input unit and the weight coefficient, and the neural network updates the weight coefficient on the basis of the comparison result between the estimated positional information output by inputting the image of the first image group and the image of the second image group and the ground truth position label associated with the input image.

In the fifth aspect, in the image learning device according to a sixth aspect, the neural network does not reflect the estimated positional information output for the image, for which the positional information acquisition unit does not acquire the positional information, among the images of the first image group, in the update of the weight coefficient.

In any one of the first to sixth aspects, in the image learning device according to a seventh aspect, the weight coefficient storage unit stores as the weight coefficient, a first weight coefficient group referred to only in a case where the first task is performed to output the classification score as the evaluation result, a second weight coefficient group referred to only in a case where the second task is performed to output the evaluation result, and a third weight coefficient group referred to in a case where any of the first task and the second task is performed.

In any one of the first to seventh aspects, in the image learning device according to an eighth aspect, the image of the first image group and the image of the second image group are images captured by the same kind of imaging device. In the eighth aspect, the term "the same kind of imaging devices" means "the same modality" such as "between the endoscope devices", and "between the ultrasonic devices", and may not be the endoscope devices of the same model.

In any one of the first to eighth aspects, in the image learning device according to a ninth aspect, the recognition target is a histological structure of a target to be imaged.

In any one of the first to ninth aspects, in the image learning device according to a tenth aspect, the image of the first image group and the image of the second image group are images acquired by an endoscope device.

An image learning method according to an eleventh aspect of the invention is an image learning method using a neural network including an input unit that inputs an image, a weight coefficient storage unit that stores a weight coefficient to be applied to the input image, and an output unit that outputs an evaluation result of the input image on the basis of the input image and the weight coefficient, the image learning method comprising acquiring a first image group composed of images each including at least one recognition target; acquiring a second image group composed of images not including the recognition target; acquiring ground truth data associated with the images; executing a first task of classifying the recognition target in the input image and outputting a classification score as the evaluation result; executing a second task different from the first task on the input image; and updating the weight coefficient on the basis of results of the first task and the second task, in which in the acquiring of the ground truth data, a ground truth classification label associated with the image of the first image group is acquired as the ground truth data, for the executing of the first task, and the ground truth data associated with the image of the first image group and the ground truth data associated with the image of the second image group are acquired for the executing of the second task, and in the updating of the weight coefficient, the weight coefficient is updated on the basis of a comparison result between the classification score output for the image of the first image group and the ground truth classification label, and the classification score output for the image of the second image group is not reflected in an update of the weight coefficient, and the weight coefficient is updated on the basis of the evaluation result output for the image of the first image group and the evaluation result output for the image of the second image group. According to the eleventh aspect, it is possible to support appropriate classification of images as in the first aspect.

The image learning method according to the eleventh aspect may further comprise the same configuration as that in the second to tenth aspects. A non-temporary recording medium in which a program causing a computer to execute the image learning method according to the aspect of the invention and a computer-readable code of such a program are recorded can also be exemplified as an aspect of the invention.

A neural network according to a twelfth aspect of the invention is a neural network learned by the image learning method according to the eleventh aspect. According to the twelfth aspect, it is possible to support appropriate classification of images as in the first and eleventh aspects.

An image classification device according to a thirteenth aspect of the invention comprises an image acquisition unit that acquires time-series images; and the neural network according to the twelfth aspect, in which the image classification device performs classification processing on the acquired images using the neural network. According to the thirteenth aspect, it is possible to support appropriate classification of images as in the first, eleventh and twelfth aspects.

BRIEF DESCRIPTION OF THE DRAWINGS

FIGS. 6A and 6B are diagrams illustrating a configuration example of a convolutional neural network.

DESCRIPTION OF THE PREFERRED EMBODIMENTS

Hereinafter, embodiments of an image learning device, an image learning method, a neural network, and an image classification device according to the invention will be described in detail with reference to the accompanying drawings.

First Embodiment

Configuration of Endoscope System

Figure 1:
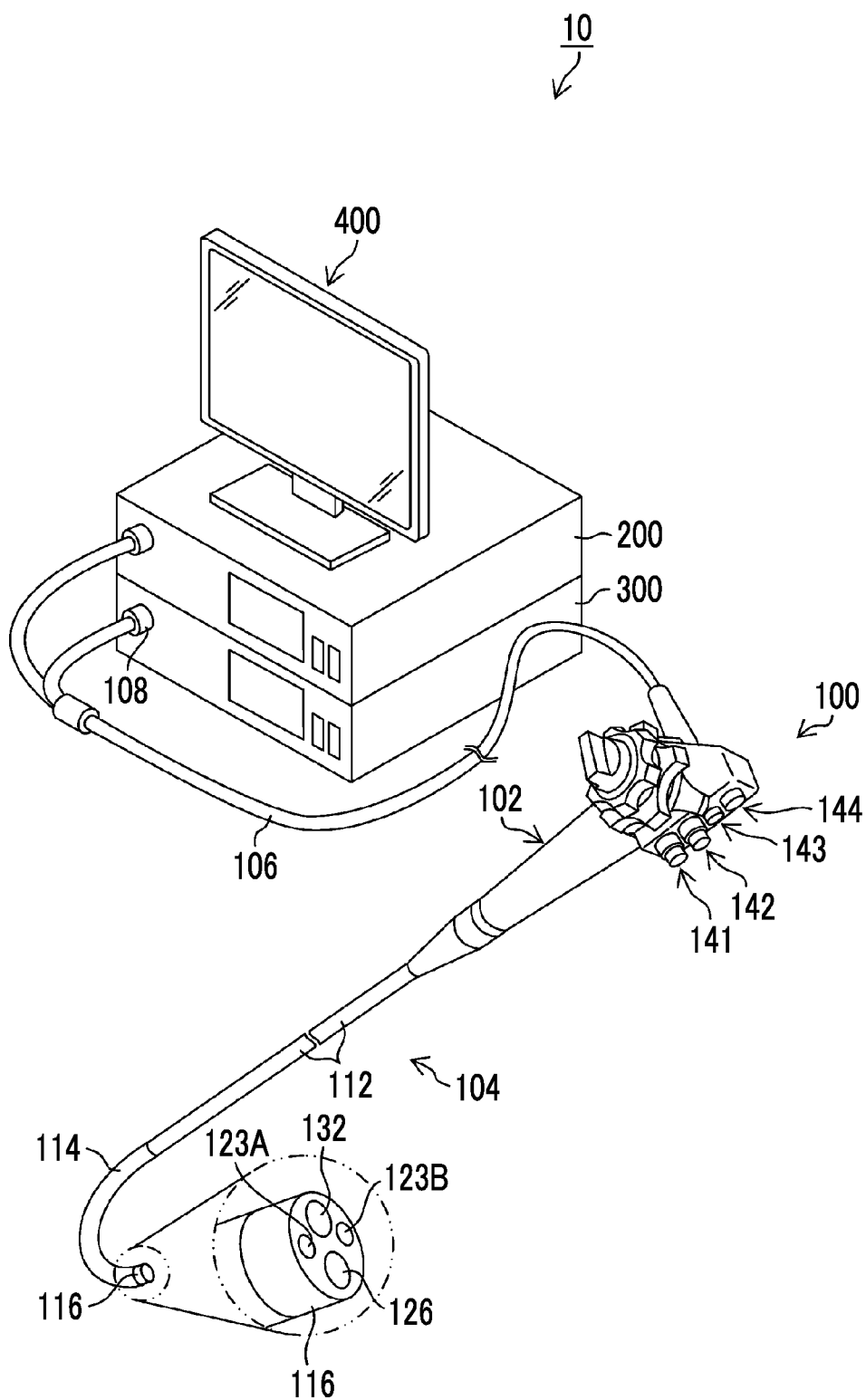
FIG. 1 is a diagram illustrating a configuration of an endoscope system according to a first embodiment.
Figure 2:
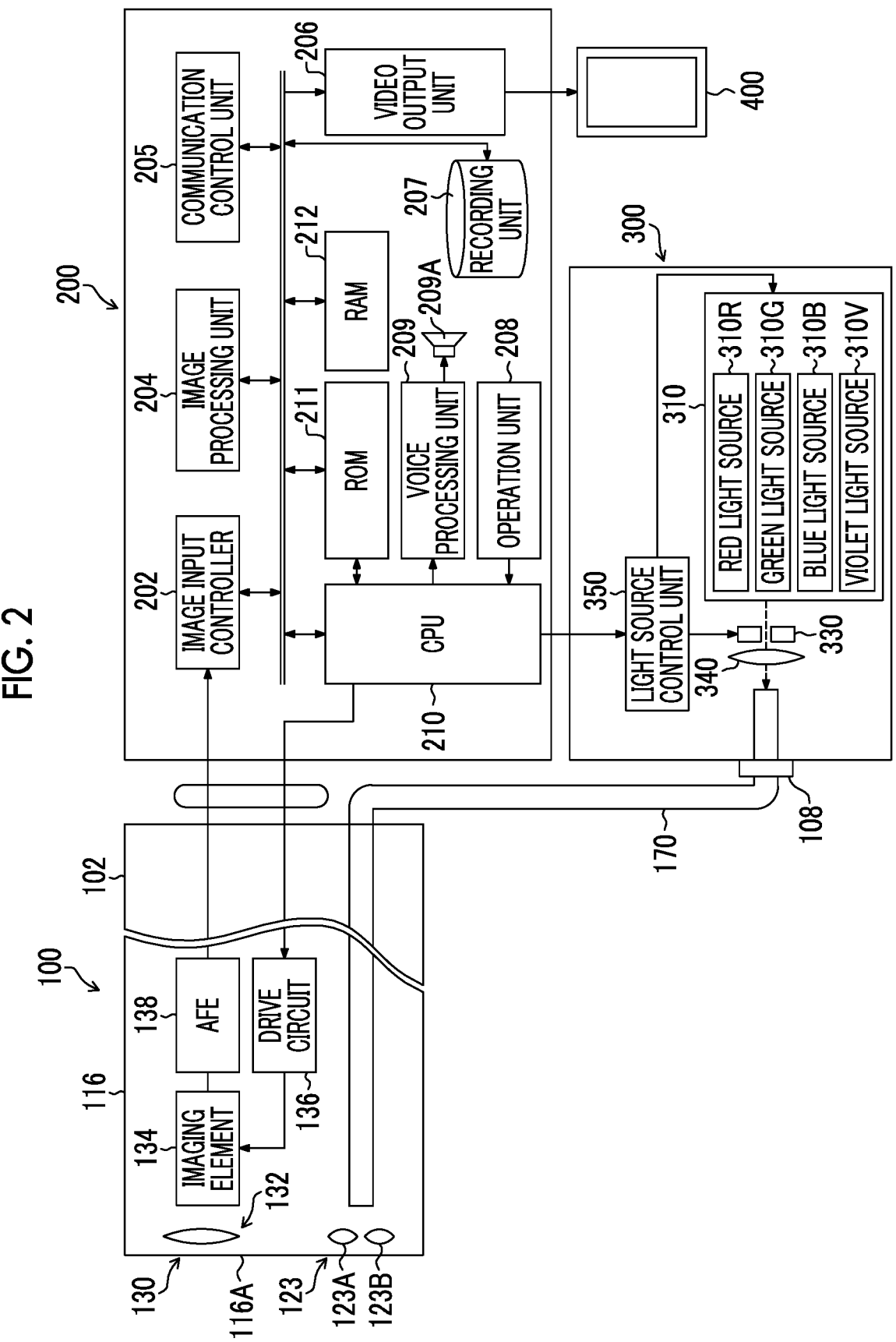
FIG. 2 is another diagram illustrating the configuration of the endoscope system.

FIG. 1 is an external view of an endoscope system 10 (endoscope device, image learning device, medical image learning device), and FIG. 2 is a block diagram illustrating a main configuration of the endoscope system 10. As illustrated in FIGS. 1 and 2, the endoscope system 10 includes an endoscope scope 100 (first image acquisition unit, second image acquisition unit, image acquisition unit, endoscope device), a processor 200 (image learning device, medical image learning device, image classification device, image acquisition unit, endoscope device), a light source device 300 (light source device), and a monitor 400 (display device).

Configuration of Endoscope Scope

The endoscope scope 100 comprises a hand operation part 102, and an insertion part 104 provided to be continuous to the hand operation part 102. An operator (user) grips and operates the hand operation part 102, inserts the insertion part 104 into a subject (living body), and observes the inside of the subject. Further, the hand operation part 102 is provided with an air/water supply button 141, a suction button 142, a function button 143 to which various functions are assigned, and an imaging button 144 that accepts an imaging instruction operation (static image, video). The insertion part 104 includes a soft portion 112, a bendable portion 114, and a hard distal end portion 116 that are arranged in this order from the hand operation part 102. That is, the bendable portion 114 is connected to the proximal end side of the hard distal end portion 116, and the soft portion 112 is connected to the proximal end side of the bendable portion 114. The hand operation part 102 is connected to the proximal end side of the insertion part 104. In a case where a user operates the hand operation part 102, the user can bend the bendable portion 114 to vertically and laterally change the direction of the hard distal end portion 116. The hard distal end portion 116 is provided with an imaging optical system 130, an illumination unit 123, a forceps port 126, and the like (refer to FIGS. 1 and 2).

In a case of observation and treatment, white light and/or narrow-band light (one or more among red narrow-band light, green narrow-band light, blue narrow-band light, and violet narrow-band light) can be applied from illumination lenses 123A and 123B of the illumination unit 123 by the operation of an operation unit 208 (refer to FIG. 2). Further, cleaning water is ejected from a water supply nozzle (not illustrated) by the operation of the air/water supply button 141, so that an imaging lens 132 (imaging lens, imaging unit) of the imaging optical system 130 and the illumination lenses 123A and 123B can be cleaned. A pipe line (not illustrated) communicates with the forceps port 126 that is open at the hard distal end portion 116, and a treatment tool (not illustrated) for the removal of a tumor or the like is inserted into the pipe line and is appropriately moved forwards and backwards to perform necessary treatments on the subject.

As illustrated in FIGS. 1 and 2, the imaging lens 132 (imaging unit) is provided on a distal end-side end face 116A of the hard distal end portion 116. A complementary-metal-oxide-semiconductor (CMOS) type imaging element 134 (imaging element, image acquisition unit), a drive circuit 136, and an analog front end (AFE, imaging unit) 138 are provided in the back of the imaging lens 132, and image signals are output by these elements. The imaging element 134 is a color image pickup element, and comprises a plurality of pixels formed of a plurality of light-receiving elements that are arranged in a matrix form (two-dimensionally arrayed) so as to have a specific pattern array (Bayer array, X-Trans (registered trademark) array, honeycomb array, or the like). Each pixel of the imaging element 134 includes a microlens, a red (R), green (G), or blue (B) color filter, and a photoelectric conversion part (photodiode or the like). The imaging optical system 130 also can generate a color image from pixel signals corresponding to three colors of red, green, and blue, and also can generate an image from pixel signals corresponding to any one color or two colors among red, green, and blue. The imaging element 134 may be a charge-coupled-device (CCD) type imaging element. Further, each pixel of the imaging element 134 may further comprise a violet color filter corresponding to a violet light source 310V and/or an infrared filter corresponding to an infrared light source.

The optical image of the subject is formed on a light-receiving surface (imaging surface) of the imaging element 134 by the imaging lens 132 and is converted into electrical signals, and the electrical signals are output to the processor 200 via a signal cable (not illustrated) and are converted into video signals. Accordingly, an endoscopic image (image, medical image) is displayed on the monitor 400 connected to the processor 200.

Further, the illumination lenses 123A and 123B of the illumination unit 123 are provided on the distal end-side end face 116A of the hard distal end portion 116 so as to be adjacent to the imaging lens 132. An emitting end of a light guide 170 to be described below is provided in the back of the illumination lenses 123A and 123B; the light guide 170 is inserted into the insertion part 104, the hand operation part 102, and a universal cable 106; and an incident end of the light guide 170 is disposed in a light guide connector 108.

The user can sequentially capture time-series images of the living body by performing imaging at a determined frame rate (which can be performed by controlling a first image acquisition unit 220 and a second image acquisition unit 222) while inserting or extracting the endoscope scope 100 (insertion part 104) having the above-described configuration into or from the living body as the subject.

Configuration of Light Source Device

As illustrated in FIG. 2, the light source device 300 includes a light source 310 for illumination, a stop 330, a condenser lens 340, a light source control unit 350, and the like, and causes observation light to be incident on the light guide 170. The light source 310 comprises a red light source 310R, a green light source 310G, a blue light source 310B, and the violet light source 310V which respectively apply red narrow-band light, green narrow-band light, blue narrow-band light, and violet narrow-band light, and can apply red narrow-band light, green narrow-band light, blue narrow-band light, and violet narrow-band light. The illuminance of observation light applied by the light source 310 is controlled by the light source control unit 350, so that the illuminance of observation light can be changed (increased or lowered) or illumination can be stopped as necessary.

The light source 310 can emit red narrow-band light, green narrow-band light, blue narrow-band light, and violet narrow-band light in any combination. For example, the light source can apply white light (normal light) as observation light by emitting red narrow-band light, green narrow-band light, blue narrow-band light, and violet narrow-band light at the same time, and can apply narrow-band light (special light) by emitting any one or two of red narrow-band light, green narrow-band light, blue narrow-band light, and violet narrow-band light. The light source 310 may further comprise an infrared light source that applies infrared light (example of narrow-band light). Further, by the light source that applies white light and filters transmitting white light and narrow-band light, white light or narrow-band light may be applied as observation light.

Wavelength Range of Light Source

The light source 310 may be a light source that generates light in a white-light wavelength range or light in a plurality of wavelength ranges as light in a white-light wavelength range, and may be a light source that generates light in a specific wavelength range narrower than the white-light wavelength range. The specific wavelength range may be a blue-light wavelength range or a green-light wavelength range of a visible-light wavelength range or a red-light wavelength range of a visible-light wavelength range. In a case where the specific wavelength range is a blue-light wavelength range or a green-light wavelength range of a visible-light wavelength range, the specific wavelength range may include a wavelength range of 390 nm to 450 nm or 530 nm to 550 nm, and light in the specific wavelength range may have a peak wavelength in a wavelength range of 390 nm to 450 nm or 530 nm to 550 nm. Further, in a case where the specific wavelength range is a red-light wavelength range of a visible-light wavelength range, the specific wavelength range may include a wavelength range of 585 nm to 615 nm or 610 nm to 730 nm, and light in the specific wavelength range may have a peak wavelength in a wavelength range of 585 nm to 615 nm or 610 nm to 730 nm.

Light in the above-described specific wavelength range may include a wavelength range where a light absorption coefficient in oxyhemoglobin is different from that in reduced hemoglobin, and may have a peak wavelength in a wavelength range where a light absorption coefficient in oxyhemoglobin is different from that in reduced hemoglobin. In this case, the specific wavelength range may include a wavelength range of 400±10 nm, 440±10 nm, 470±10 nm, or 600 nm to 750 nm, and light in the specific wavelength range may have a peak wavelength in a wavelength range of 400±10 nm, 440±10 nm, 470±10 nm, or 600 nm to 750 nm.

Further, light generated by the light source 310 may include a wavelength range of 790 nm to 820 nm or 905 nm to 970 nm, and may have a peak wavelength in a wavelength range of 790 nm to 820 nm or 905 nm to 970 nm.

Further, the light source 310 may comprise a light source that applies excitation light having a peak wavelength in a wavelength range of 390 nm to 470 nm. In this case, a medical image (image for medical use, in-vivo image), which has information about the fluorescence of a fluorescent material present in the subject (living body), can be acquired. A pigment for a fluorescence method (fluorescein, acridine orange, or the like) may be used to acquire a fluorescence image.

It is preferable that the type (laser light source, xenon light source, light-emitting-diode (LED) light source, and the like) and wavelength of the light source 310, the presence or absence of a filter, and the like are configured according to the type of a subject, a site, the purpose of observation, and the like. Further, it is preferable that the wavelengths of observation light are combined and/or switched according to the type of a subject, a site, the purpose of observation, and the like in a case of observation. In a case where the wavelengths are to be switched, for example, a disc-shaped filter (rotary color filter) provided with filters, which are disposed in front of a light source and transmit or block light having specific wavelengths, may be rotated to switch the wavelength of light to be applied.

Furthermore, an imaging element, which is used to embody the invention, is not limited to a color imaging element where a color filter is provided for each pixel as with the imaging element 134, and may be a monochromatic imaging element. In a case where a monochromatic imaging element is used, imaging can be performed in order of surface (in order of color) while the wavelengths of observation light are sequentially switched. For example, the wavelengths of observation light to be emitted may be sequentially switched among rays of narrow-band light (violet, blue, green, red); and broadband light (white light) may be applied and the wavelengths of observation light to be emitted may be switched by the rotary color filter (red, green, blue, violet, and the like). Moreover, one or a plurality of rays of narrow-band light (green, blue, violet, and the like) may be applied, and the wavelengths of observation light to be emitted may be switched by the rotary color filter (green, blue, violet, and the like). The narrow-band lights may be infrared light (first narrow-band light, second narrow-band light) having two or more different wavelengths.

The light guide connector 108 (refer to FIGS. 1 and 2) is connected to the light source device 300, so that observation light applied from the light source device 300 is transmitted to the illumination lenses 123A and 123B via the light guide 170 and is applied to an observation range from the illumination lenses 123A and 123B.

Configuration of Processor

The configuration of the processor 200 will be described with reference to FIG. 2. The image signals output from the endoscope scope 100 are input to the processor 200 via an image input controller 202, and the processor 200 performs necessary image processing on the image signals by an image processing unit 204 (medical image processing unit) and outputs the resultant signals via a video output unit 206. Accordingly, an observation image (in-vivo image) is displayed on the monitor 400 (display device). These kinds of processing are performed under the control of a central processing unit (CPU) 210. A communication control unit 205 performs communication control for medical images or site information with a hospital information system (HIS), a hospital local area network (LAN), and/or an external system or network (not illustrated).

Functions of Image Processing Unit

Figure 3:
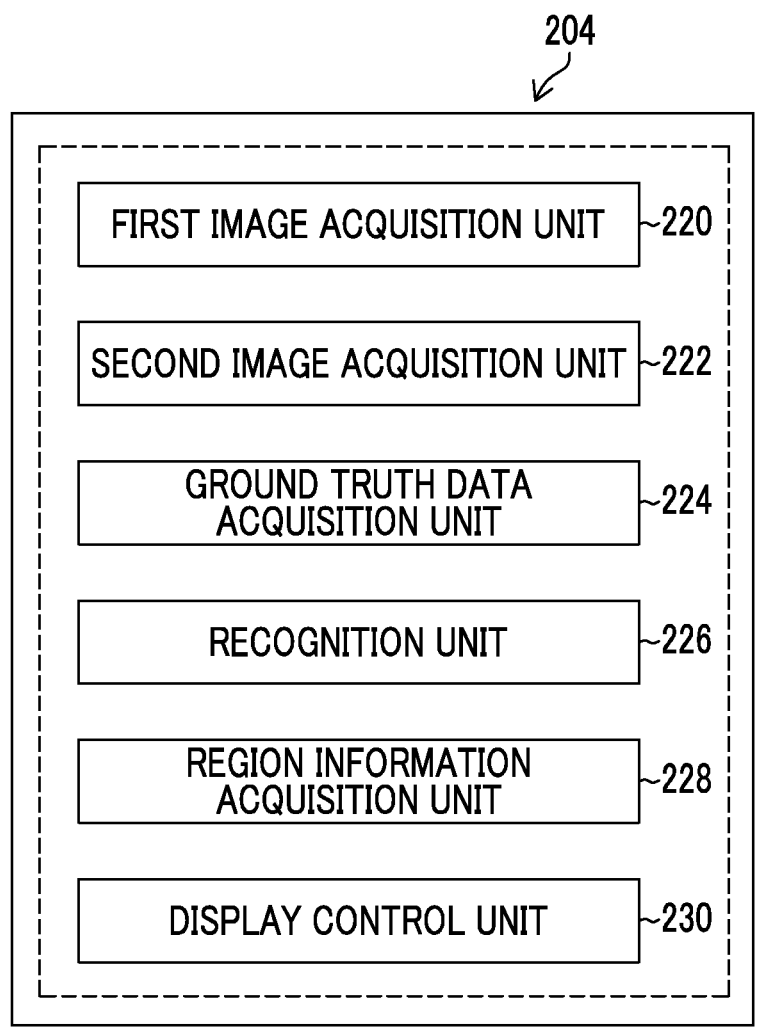
FIG. 3 is a functional block diagram of an image processing unit.

FIG. 3 is a functional block diagram of the image processing unit 204. The image processing unit 204 comprises the first image acquisition unit 220 (first image acquisition unit, image acquisition unit), the second image acquisition unit 222 (second image acquisition unit, image acquisition unit), a ground truth data acquisition unit 224 (ground truth data acquisition unit, ground truth segmentation label generation unit), a recognition unit 226 (neural network), a region information acquisition unit 228 (region information acquisition unit), and a display control unit 230. Details of learning and classification of images using the functions will be described below.

The image processing unit 204 can perform calculation of a feature quantity of medical images, processing of emphasizing or reducing components in a specific frequency band, and processing of emphasizing or obscuring a specific target (region of interest, blood vessel at desired depth, and the like), using the above-described functions. The image processing unit 204 may comprise a special light image acquisition unit that acquires a special light image having information about a specific wavelength range on the basis of a normal light image obtained from the application of light in a white-light wavelength range or light in a plurality of wavelength ranges as the light in a white-light wavelength range. In this case, a signal in the specific wavelength range can be obtained from an arithmetic operation based on color information about RGB (R: red, G: green, and B: blue) or CMY (C: cyan, M: magenta, and Y: yellow) included in the normal light image. Further, the image processing unit 204 may comprise a feature quantity image generation unit which generates a feature quantity image from an arithmetic operation based on at least one of a normal light image that is obtained from the application of light in a white-light wavelength range or light in a plurality of wavelength ranges as the light in a white-light wavelength range and a special light image that is obtained from the application of light in a specific wavelength range, and may acquire and display the feature quantity image as the medical image (image for medical use). The above-described processing is performed under the control of CPU 210.

Realization of Functions by Various Processors

The functions of respective units of the above-described image processing unit 204 can be realized using various processors and recording mediums. The various processors include a central processing unit (CPU) that is a general-purpose processor realizing various functions by executing software (program), for example. Further, the above-described various processors also include a graphics processing unit (GPU) that is specialized for image processing, and a programmable logic device (PLD) that is a processor of which the circuit configuration can be changed after manufacture, such as a field programmable gate array (FPGA). In a case of performing learning and recognition of images as in the invention, a configuration using the GPU is effective. Furthermore, the above-described various processors also include dedicated electrical circuitry, which is a processor having a circuit configuration designed exclusively to execute specific processing, such as an application specific integrated circuit (ASIC).

The functions of the respective units may be realized by one processor, or may be realized by the same or different kinds of two or more processors (for example, combination of a plurality of FPGAs, combination of the CPU and the FPGA, or combination of the CPU and the GPU). Further, a plurality of functions may be realized by one processor. As an example where a plurality of functions are configured by one processor, first, there is a form where one processor is configured of a combination of one or more CPUs and software as typified by a computer, and this processor realizes the plurality of functions. Second, there is a form where a processor realizing the functions of the entire system by one integrated circuit (IC) chip as typified by System On Chip (SoC) or the like is used. In this way, various functions are configured using one or more of the above-described various processors as hardware structures. Furthermore, the hardware structures of these various processors are more specifically electrical circuitry where circuit elements, such as semiconductor elements, are combined. The electrical circuitry may be an electrical circuitry that realizes the above-described functions using logical sum, logical product, logical negation, exclusive OR, and logical operation obtained by the combination thereof.

In a case where the above-described processor or electrical circuitry is to execute software (program), codes, which can be read by a computer (for example, various processors and electrical circuitry constituting the image processing unit 204, and/or a combination thereof) of the software to be executed are stored in a non-temporary recording medium such as a read only memory (ROM) 211, and the computer refers to the software. The software stored in the non-temporary recording medium includes programs for executing a medical image processing method according to an embodiment of the invention, and data used for execution (data regarding acquisition of site information, data used for specifying a display aspect, parameter used in a recognizer, and the like). The codes may be recorded in a non-temporary recording medium such as various magneto-optical recording devices and semiconductor memories, instead of the ROM 211. In a case where processing is to be performed using software, for example, a random access memory (RAM) 212 is used as a temporary storage region, and the data stored in, for example, an electronically erasable and programmable read only memory (EEPROM) (not illustrated) can be referred to. A recording unit 207 may be used as the "non-temporary recording medium".

Furthermore, the read only memory (ROM) 211 is a non-volatile storage element (non-temporary recording medium), and stores computer-readable codes of a program causing the CPU 210 and/or the image processing unit 204 (computer) to execute various image processing methods, image learning methods, and image classification methods (including an image learning method and an image classification method according to an embodiment of the invention). The random access memory (RAM) 212 is a storage element for temporary storage in a case of performing various kinds of processing, and can also be used as a buffer during image acquisition.

A voice processing unit 209 outputs a message (voice) regarding learning, classification, and the like from a speaker 209A under the control of the CPU 210 and the image processing unit 204. In addition, the user can perform an instruction for execution of image learning and designation of necessary conditions for execution via the operation unit 208, and the display control unit 230 can display a screen in the case of the instructions, recognition results, and the like on the monitor 400.

Figure 4:
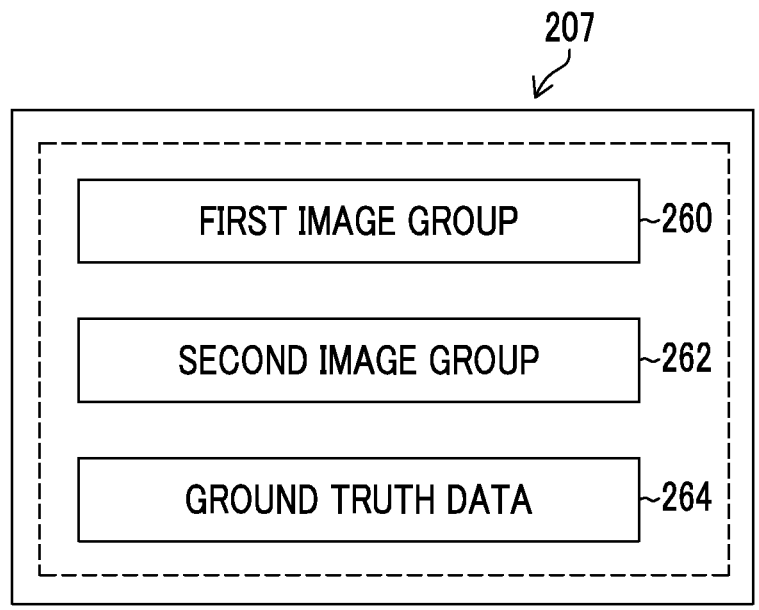
FIG. 4 is a diagram illustrating information recorded in a recording unit.

As illustrated in FIG. 4, a first image group 260 (endoscopic image, medical image, image for medical use), a second image group 262 (endoscopic image, medical image, image for medical use), ground truth data 264, and the like are recorded in the recording unit 207 (recording device). In the first embodiment, the ground truth data 264 includes ground truth classification labels (ground truth data) associated with the images of the first image group, and ground truth segmentation labels (ground truth data) associated with the images of the first image group and the images of the second image group. The recording unit 207 may record the region information (mask image of a recognition target) in association with the images of the first image group, in addition to those pieces of data.

Recognition Unit by Neural Network

In the first embodiment, the recognition unit 226 performs a first task (classification) of classifying the recognition target in the input image and outputting a classification score as an evaluation result, and a second task (segmentation) of outputting a segmentation score as an evaluation result for each small region of the image, in the process of image learning. The first task and the second task can be performed using a learned model (model learned using an image set including images of obtained by imaging living body) such as the neural network. Hereinafter, a configuration using a convolutional neural network as the neural network will be described.

Configuration Example of Recognition Unit

Figure 5:
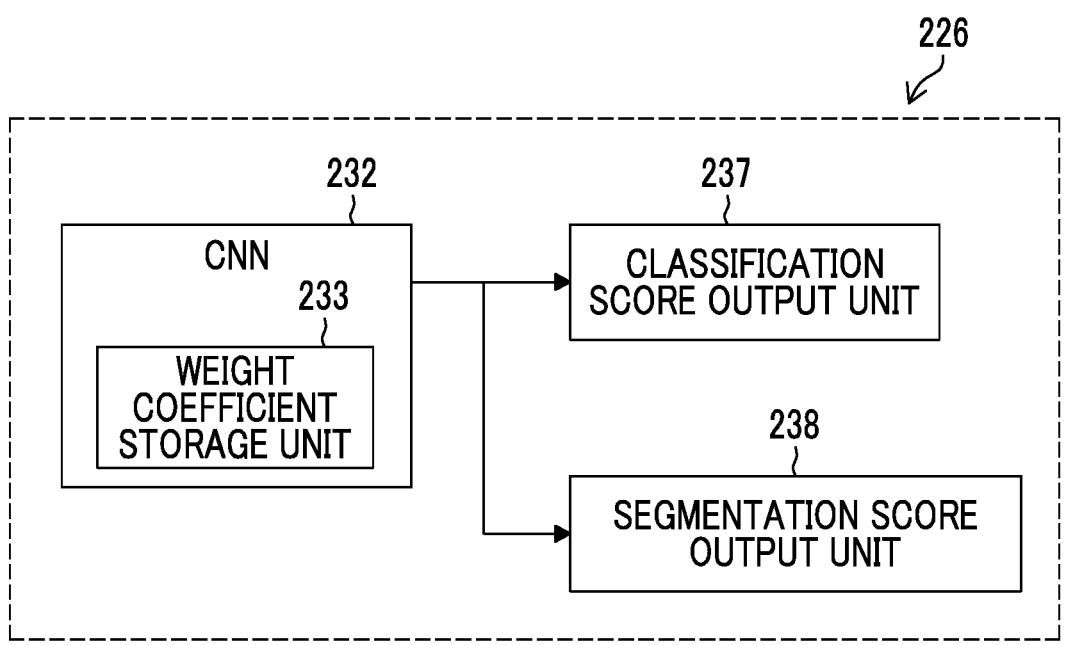
FIG. 5 is a diagram illustrating a configuration of a recognition unit.

FIG. 5 is a diagram illustrating the configuration of the recognition unit 226 according to the first embodiment. In the example illustrated in FIG. 5, the recognition unit 226 (neural network) comprises a CNN 232 (neural network), a classification score output unit 237 (neural network, output unit), and a segmentation score output unit 238 (neural network, output unit). The CNN 232 has a weight coefficient storage unit 233 (weight coefficient storage unit).

FIGS. 6A and 6B are diagrams illustrating a configuration of the CNN 232. In the example illustrated in FIG. 6A, the CNN 232 has an input layer 232A (input unit), an intermediate layer 232B, and an output layer 232C. The input layer 232A receives endoscopic images (image, medical image) acquired by the first image acquisition unit 220 and the second image acquisition unit 222 and outputs a feature quantity. The intermediate layer 232B includes a convolutional layer 234 and a pooling layer 235, and receives the feature quantity output from the input layer 232A to calculate other feature quantities. These layers have a structure in which a plurality of "nodes" are connected by "edges", a weight coefficient to be applied to the input image is stored in association with the node and edge, in the weight coefficient storage unit 233 (weight coefficient storage unit; refer to FIG. 5). The value of the weight coefficient changes as the learning progresses.

Processing in Intermediate Layer

The intermediate layer 232B calculates a feature quantity by convolution operations and pooling processing. The convolution operation performed by the convolutional layer 234 is processing of acquiring a feature map by the convolution operation using filters, and plays a role of feature extraction such as edge extraction or the like from the image. By the convolution operation using filters, a "feature map" of one channel (one sheet) is generated for one filter. In a case where the size of the "feature map" is downscaled by convolution, the size is reduced as the convolution is performed on each layer. The pooling processing performed by the pooling layer 235 is processing of reducing (or expanding) the feature map output by the convolution operation to a new feature map, and plays a role of giving robustness so that the extracted features are not affected by translation or the like. The intermediate layer 232B can be configured by one or a plurality of layers performing the processing. The CNN 232 may be configured without the pooling layer 235.

As in the example illustrated in FIG. 6B, the CNN 232 may include a fully connected layer 236. The layer configuration of the CNN 232 is not limited to a case where the convolutional layers 234 and the pooling layers 235 are repeated one by one, and may include a plurality of any layers (for example, convolutional layer 234) continuously.

Figure 7:
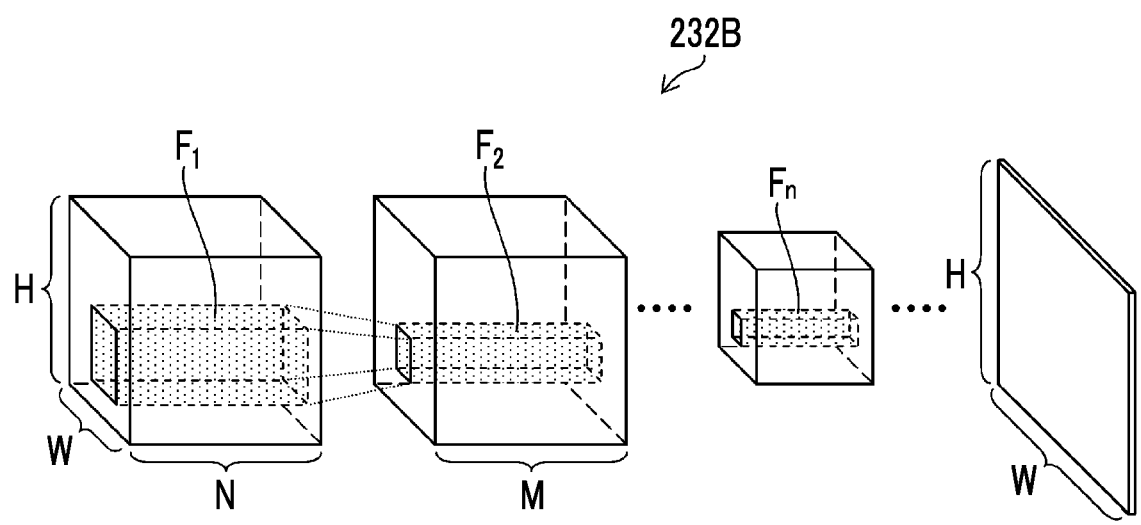
FIG. 7 is a diagram illustrating a state of convolution processing using filters.

FIG. 7 is a schematic diagram illustrating a configuration example of the intermediate layer 232B of the CNN 232 illustrated in FIGS. 6A and 6B. In the first convolutional layer of the intermediate layer 232B, the convolution operation between an image set (learning image set during learning, recognition image set during recognition) composed of a plurality of medical images and a filter $F_1$ is performed. The image set is composed of N (N channels) images having an image size of H in a vertical direction and W in a horizontal direction. In a case where normal light images are input, images constituting the image set are images of three channels of red (R), green (G), and blue (B). Since the image sets are N channels (N sheets), the filter $F_1$ used in the convolution operation with the image set has a filter size of 5×5×N in a case of a filter having a size 5 (5×5). By the convolution operation using the filter $F_1$, a "feature map" of one channel (one sheet) is generated for one filter $F_1$. A filter $F_2$ used in the second convolutional layer has a filter size of 3×3×M in a case of a filter having a size 3 (3×3).

As in the first convolutional layer, in the second to n-th convolutional layers, convolution operation is performed using filters $F_2$ to $F_n$. The size of the "feature map" in the n-th convolutional layer is smaller than the size of the "feature map" in the second convolutional layer because the feature map is downscaled by the convolutional layer or the pooling layer up to the preceding stage.

Among the layers of the intermediate layer 232B, low-level feature extraction (edge extraction or the like) is performed in the convolutional layer close to the input side, and high-level feature extraction (feature extraction regarding the shape, structure, and the like of the recognition target) is performed as approaching the output side.

The intermediate layer 232B may include a layer for batch normalization in addition to the convolutional layer 234 and the pooling layer 235. The batch normalization processing is processing of normalizing data distribution in units of mini-batch in a case of performing learning, and plays a role of speeding up learning, reducing dependence on initial values, suppressing overlearning, and the like.

The output layer 232C outputs the feature quantity calculated by the intermediate layer 232B in a format suitable for the calculation of the classification score and the segmentation score. The output layer 232C may include a fully connected layer.

Classification Score Output Unit and Segmentation Score Output Unit

The classification score output unit 237 (output unit) and the segmentation score output unit 238 (output unit) are layers that evaluate the input medical image (normal light image, special light image) and output the evaluation result (classification score, segmentation score) on the basis of the feature quantity output from the output layer 232C of the CNN 232.

Classification Score Output Unit

The classification score output unit 237 executes classification (discrimination) regarding a lesion and outputs a classification score. For example, the classification score output unit 237 may classify the endoscopic image into two categories of "neoplastic" and "non-neoplastic", may output two classification scores (the sum of the two scores is 100%) corresponding to the "neoplastic" and the "non-neoplastic" as the classification result, and may output the classification result in a case where the classification can be clearly made from the two classification scores. The classification score output unit 237 may or may not include a fully connected layer as one or a plurality of final layers. Further, upscaling is not essential. The classification score output unit 237 may classify the endoscopic image by disease type such as "hyperplastic polyp", "adenoma", and "cancer", and may classify the endoscopic image into "NICE 1", "NICE 2", and "NICE 3", according to the categories of "endoscopic findings classification of colorectal lesions". Further, the classification score output unit 237 may perform classification regarding not only a lesion but also a treatment tool (for example, biopsy forceps, snare, or syringe) shown in the image.

Segmentation Score Output Unit

The segmentation score output unit 238 can evaluate whether the image belongs to the region of interest for each small region of the endoscopic image, on the basis of the above-described "feature map", and output the evaluation result (segmentation score). The segmentation score output unit 238 may perform upscaling of the "feature map" to acquire a "feature map" having the same size as the input image set, or may perform segmentation with a low resolution without performing upscaling. That is, in a case where learning is performed with the ground truth data having the same level scale, upscaling is not necessary.

Classification and Segmentation by CNN

Figure 8:
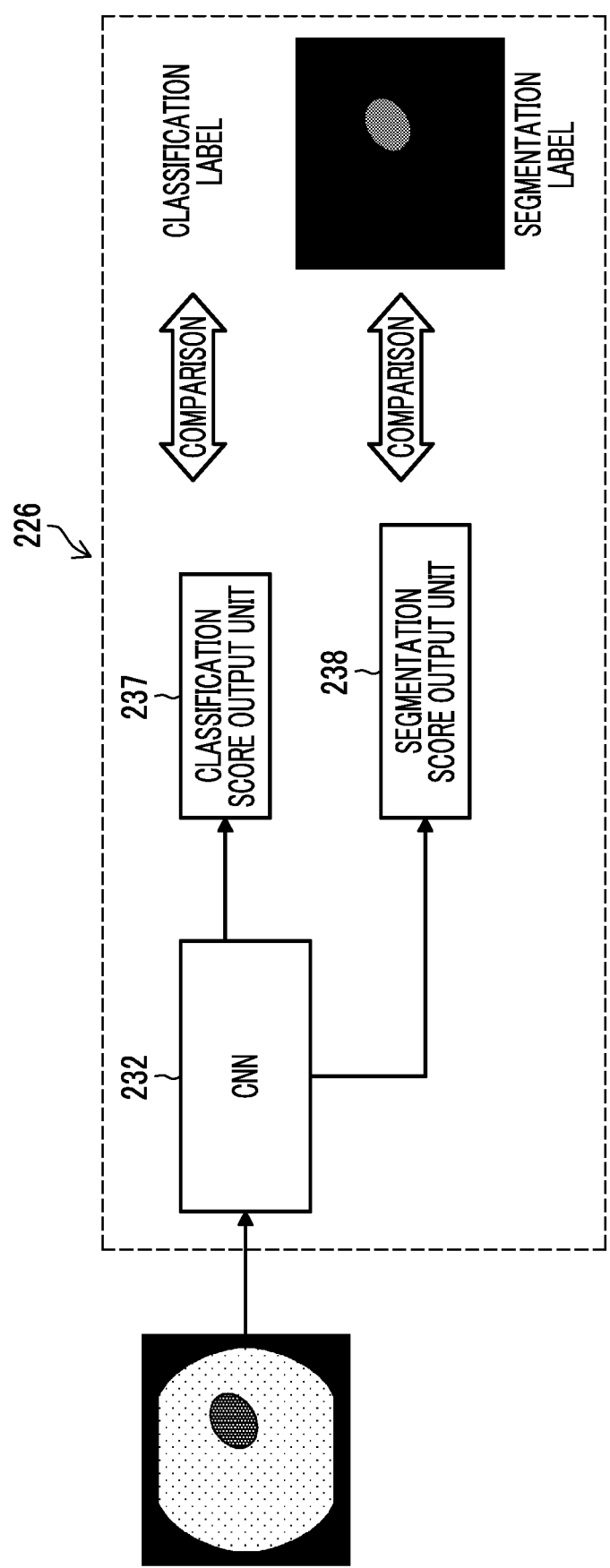
FIG. 8 is a diagram illustrating a state of learning in a case where an image includes a recognition target.
Figure 9:
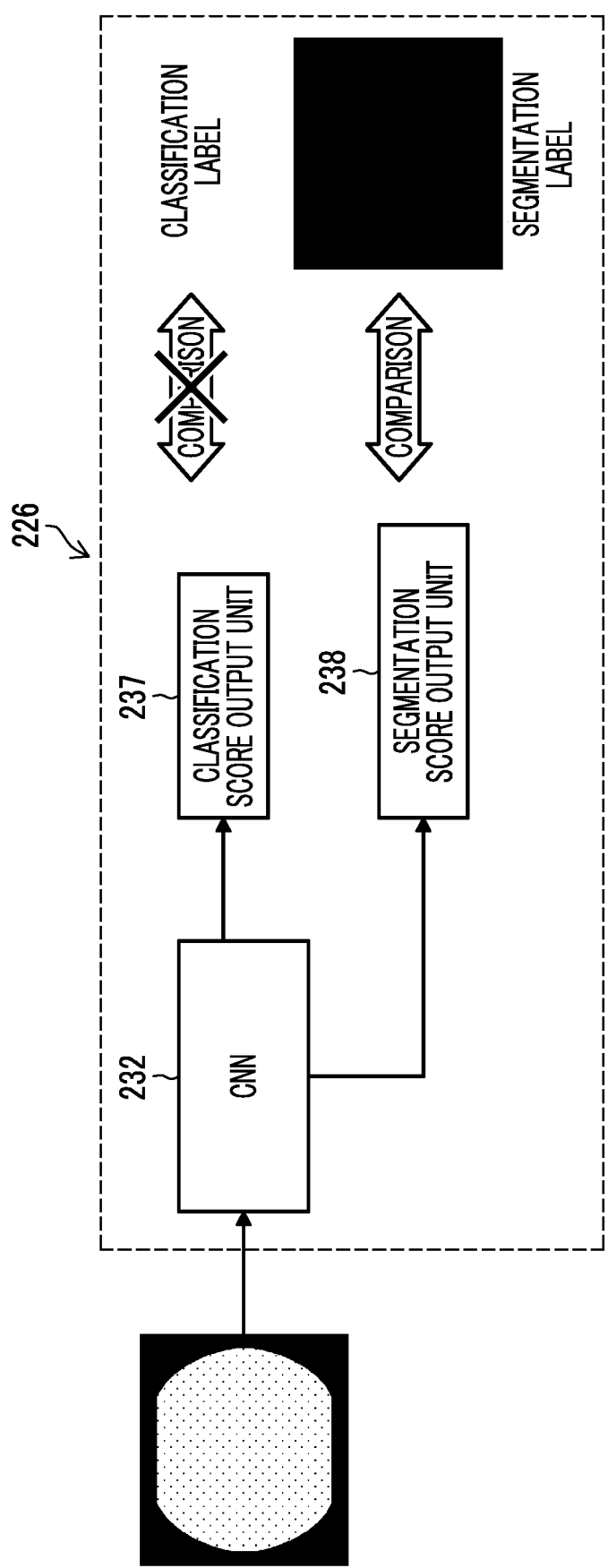
FIG. 9 is a diagram illustrating a state of learning in a case where an image does not include a recognition target.

In the first embodiment, the CNN 232 is provided with the classification score output unit 237 and the segmentation score output unit 238, and classification and segmentation are learned using the same neural network (refer to FIG. 5). FIG. 8 is a conceptual diagram illustrating a state of learning in a case where a recognition target (region of interest or the like, histological structure of living body as the target to be imaged) is included, and FIG. 9 is a conceptual diagram illustrating a state of learning in a case where the recognition target is not included. In the case of an image including a recognition target, as illustrated in FIG. 8, segmentation is learned such that a region of the recognition target in the image is classified into a corresponding class of predetermined classes, and segmentation is learned such that a region different from the recognition target is classified into a background class (predetermined class) that does not belong to any of the predetermined classes. On the other hand, for the image not including the recognition target, as illustrated in FIG. 9, segmentation is learned such that all of the regions are classified into the background class. By performing learning in this manner, for the image not including the recognition target, the background class is output in the inference processing of segmentation, and therefore, the problem that "an incorrect result is output for the image not including the recognition target" described in "SUMMARY OF THE INVENTION" can be solved.

Processing of Image Learning Method

Figure 10:
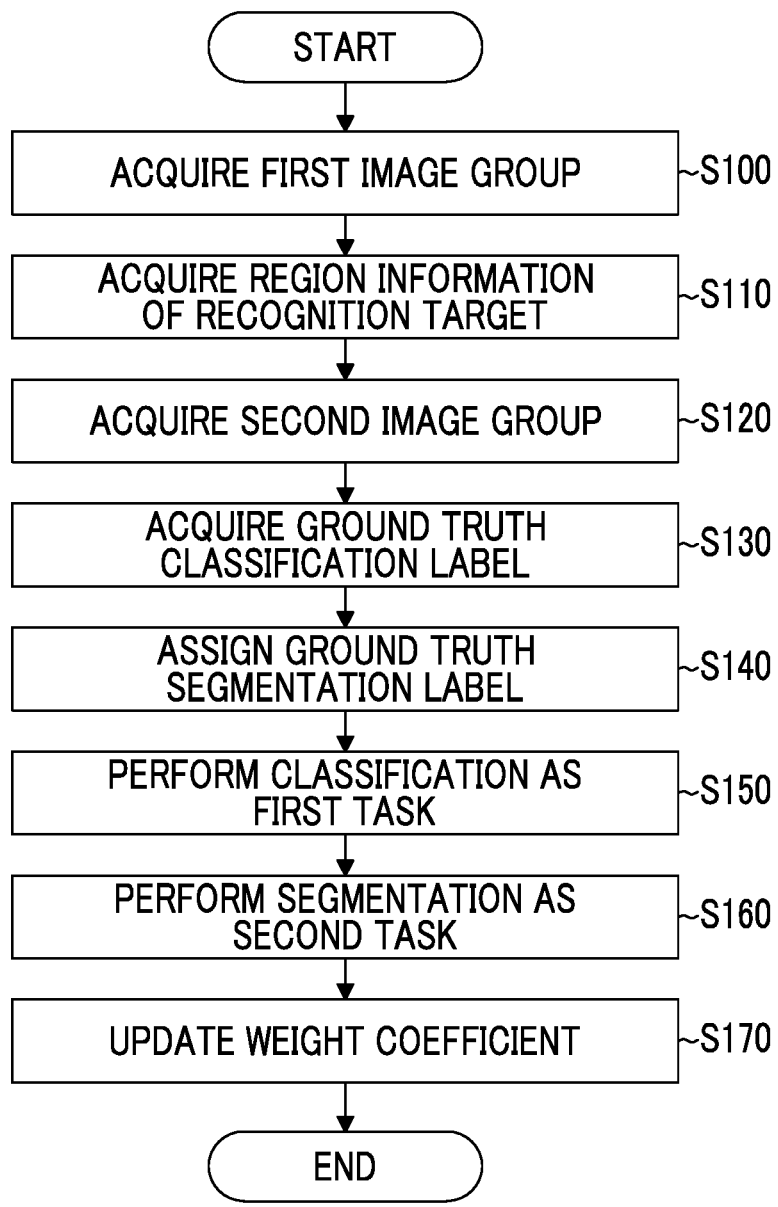
FIG. 10 is a flowchart illustrating processing of an image learning method according to the first embodiment.

FIG. 10 is a flowchart illustrating an outline of processing of an image learning method (medical image learning method) according to the first embodiment.

Acquisition of Image and Region Information

The first image acquisition unit 220 acquires a first image group composed of images each including at least one recognition target (Step S100: first image acquisition step). The "recognition target (object)" is a histological structure of a living body as a target to be imaged (for example, a region of interest such as a lesion or a region with a potential lesion). The region information acquisition unit 228 acquires region information about the recognition target in the image, for at least one image of the first image group (Step S110: region information acquisition step). The "region information" is a mask image of the object, and in the first embodiment, the region information is acquired for each image of the first image group. The region information acquisition unit 228 may acquire the region information stored in the recording unit 207, or may acquire the region information from a recording device (not illustrated) via the communication control unit 205.

Further, the second image acquisition unit 222 acquires a second image group composed of images not including the recognition target (Step S120: second image acquisition step). The images of the first image group and the images of the second image group are images acquired by the endoscope device, and have the same modality (in this case, which means "between the endoscope devices", and may not be the endoscope devices of the same model). The first image acquisition unit 220 and the second image acquisition unit 222 may acquire images of the first image group 260 and the second image group 262 recorded in the recording unit 207, or may acquire images from a recording device (not illustrated) via the communication control unit 205 and the network.

Acquisition of Ground Truth Data

The ground truth data acquisition unit 224 (ground truth data acquisition unit) acquires ground truth classification labels (ground truth data) associated with the images of the first image group for the classification as the first task (Step S130: ground truth classification label acquisition step, ground truth data acquisition step). The ground truth classification label is a "tumor" or a "non-tumor", for example. The ground truth data acquisition unit 224 may acquire the ground truth classification labels recorded in the recording unit 207, or may acquire the ground truth classification labels via the communication control unit 205 and the network.

The ground truth data acquisition unit 224 (ground truth segmentation label generation unit) generates, as the ground truth data, ground truth segmentation labels (ground truth data) associated with the images, for the image, for which the region information is acquired, among the images of the first image group and the image of the second image group (Step S140: ground truth segmentation label generation step, ground truth data acquisition step). The details of processing of generating the ground truth segmentation label will be described below.

Classification and Segmentation

The recognition unit 226 (neural network) classifies the recognition target in the input image in Step S150 (first task execution step), and the classification score output unit 237 outputs the classification score as the evaluation result (first task). Further, the recognition unit 226 (neural network) performs segmentation (second task different from the first task) on the basis of the input image and the weight coefficient, in Step S160 (second task execution step), and the segmentation score output unit 238 outputs the segmentation score as the evaluation result for each small region of the image.

Update of Weight Coefficient

The recognition unit 226 (neural network) updates the weight coefficient on the basis of the results of the first task (classification) and the second task (segmentation) (Step S170: weight coefficient update step). The details of the weight coefficient update will be described below.

Details of Processing of Generating and Assigning Segmentation Label

Figure 11:
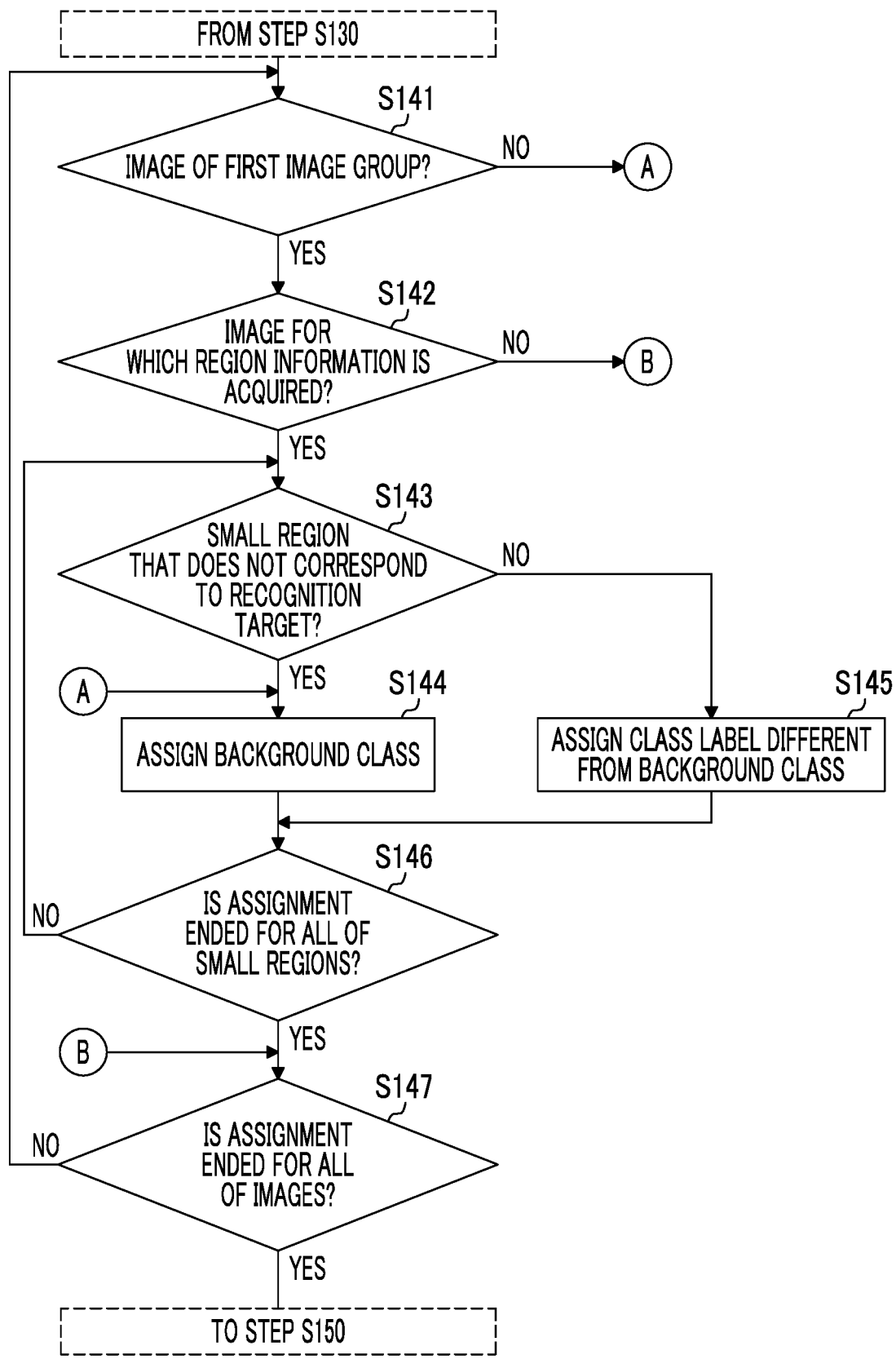
FIG. 11 is a flowchart illustrating generation processing of a segmentation label.

FIG. 11 is a flowchart illustrating details of processing of generating and assigning the segmentation label in Step S140. The recognition unit 226 determines whether the processing target image is the image of the first image group (Step S141). In a case where the processing target image is the image of the first image group, the processing proceeds to Step S142, and in a case where the processing target image is not the image of the first image group (in a case where the processing target image is the image of the second image group), the processing proceeds to Step S144. In Step S142, the recognition unit 226 determines whether the processing target image is the image for which the region information (mask image of the recognition target) is acquired in Step S110. In a case where the processing target image is the image for which the region information is acquired, the processing proceeds to Step S143, and in a case where the processing target image is not the image for which the region information is acquired, the processing proceeds to Step S147 without assigning a ground truth segmentation label.

In Step S143 (in a case where the processing target image is the image for which the region information is acquired), the recognition unit 226 determines whether a processing target small region in the image is a small region that does not correspond to the recognition target. In a case where the processing target small region is the small region that does not correspond to the recognition target (YES in Step S143), the processing proceeds to Step S144, and the background class is assigned as the ground truth segmentation label. In a case where the processing target small region is the small region that corresponds to the recognition target (NO in Step S143), the processing proceeds to Step S145, and a class label different from the background class is assigned as the ground truth segmentation label. The ground truth segmentation label may have a lower resolution than the resolution of the input image. Also in a case where the processing target image is the image of the second image group (NO in Step S141), the recognition unit 226 assigns the background class as the ground truth segmentation label in Step S144.

The recognition unit 226 repeats the processing of Steps S143 to S145 until the assignment of the ground truth segmentation label is ended for all of the small regions (until YES in Step S146). Further, the recognition unit 226 repeats the processing of Steps S141 to S146 until the assignment of the ground truth segmentation label is ended for all of the images (until YES in Step S147).

Update of Weight Coefficient

Figure 12:
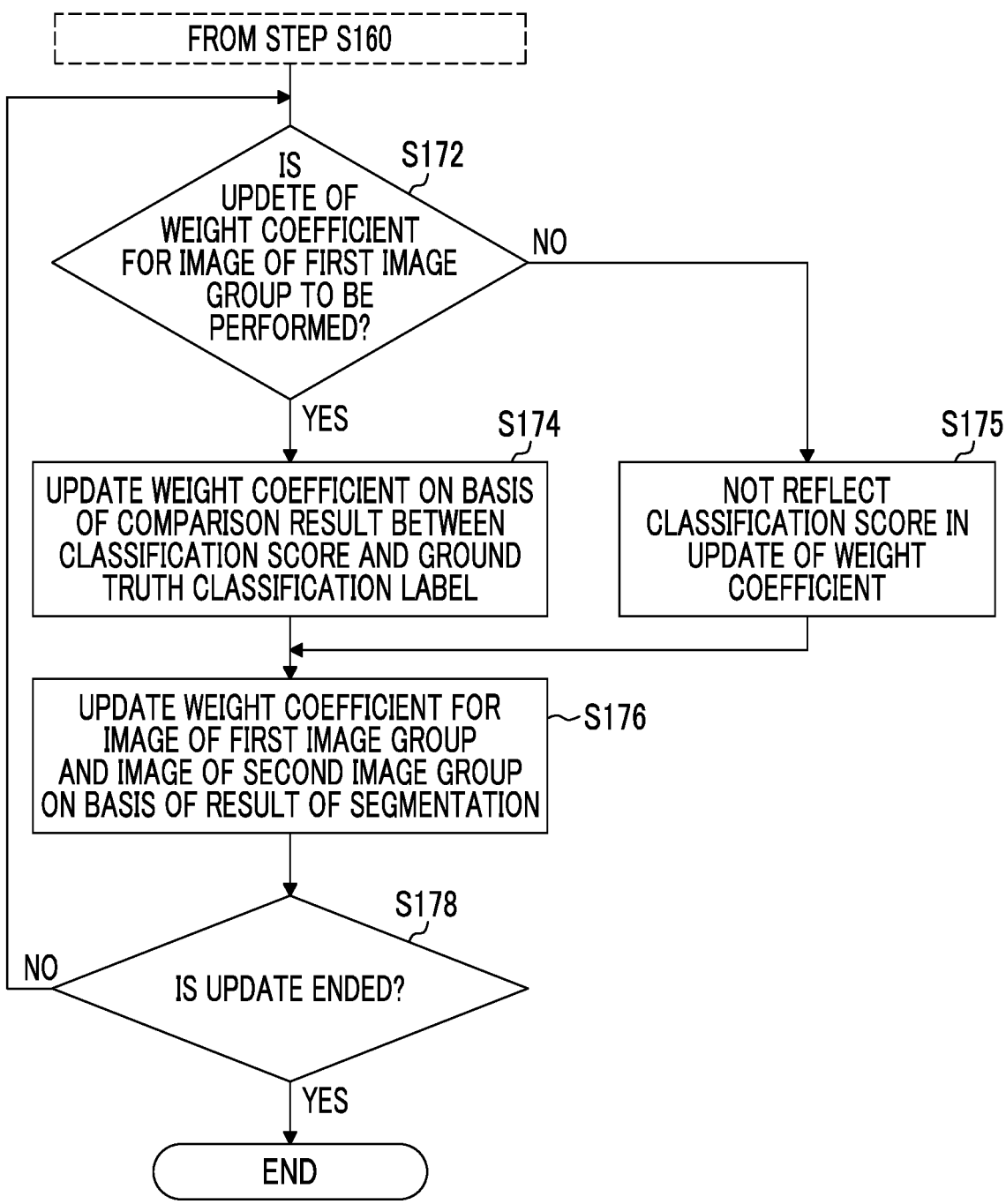
FIG. 12 is a flowchart illustrating update processing of a weight coefficient.

FIG. 12 is a flowchart illustrating details of update processing of a weight coefficient in Step S170. Steps S172 to S175 relate to the update of the weight coefficient for the result of the first task (classification), and Step S176 relates to the update of the weight coefficient for the result of the second task (segmentation).

Update of Weight Coefficient for First Task (Classification)

The recognition unit 226 determines whether the update of the weight coefficient for the image of the first image group is to be performed (Step S172: weight coefficient update step). In a case where the update of the weight coefficient for the image of the first image group is to be performed (YES in Step S172), the processing proceeds to Step S174, and the recognition unit 226 updates a weight coefficient on the basis of a comparison result between the ground truth classification label and the classification score output for the image of the first image group (weight coefficient update step; refer to the point where the output of the classification score output unit 237 is compared with the ground truth classification label in FIG. 8). On the other hand, in a case of the image (image not including the recognition target) of the second image group (NO in Step S172), the processing proceeds to Step S175, and the recognition unit 226 does not reflect the classification score output for the image of the second image group in the update of the weight coefficient (weight coefficient update step; refer to the point where the output of the classification score output unit 237 is not compared with the ground truth classification label in FIG. 9).

Update of Weight Coefficient for Second Task (Segmentation)

The recognition unit 226 updates a weight coefficient for the image of the first image group and the image of the second image group on the basis of the result of the segmentation (evaluation result) (Step S176: weight coefficient update step). Specifically, the recognition unit 226 updates the weight coefficient on the basis of a comparison result between the segmentation score output for the image of the first image group and the image of the second image group and the ground truth segmentation label associated with the input image (refer to the point where the output of the segmentation score output unit 238 is compared with the ground truth segmentation label in FIGS. 8 and 9). The recognition unit 226 repeats the processing of Steps S172 to S176 until the update of the weight coefficient is ended (until YES in Step S178).

The update of the weight coefficient may be batch processing (weight coefficients are updated in a batch mode after the first and second tasks are executed for all of the images), may be mini-batch processing (weight coefficients are updated each time the first and second tasks are executed for some of the images), or may be sequential processing (weight coefficient is updated each time the first and second tasks are executed for one image).

Modification Example of First Embodiment

Figure 13:
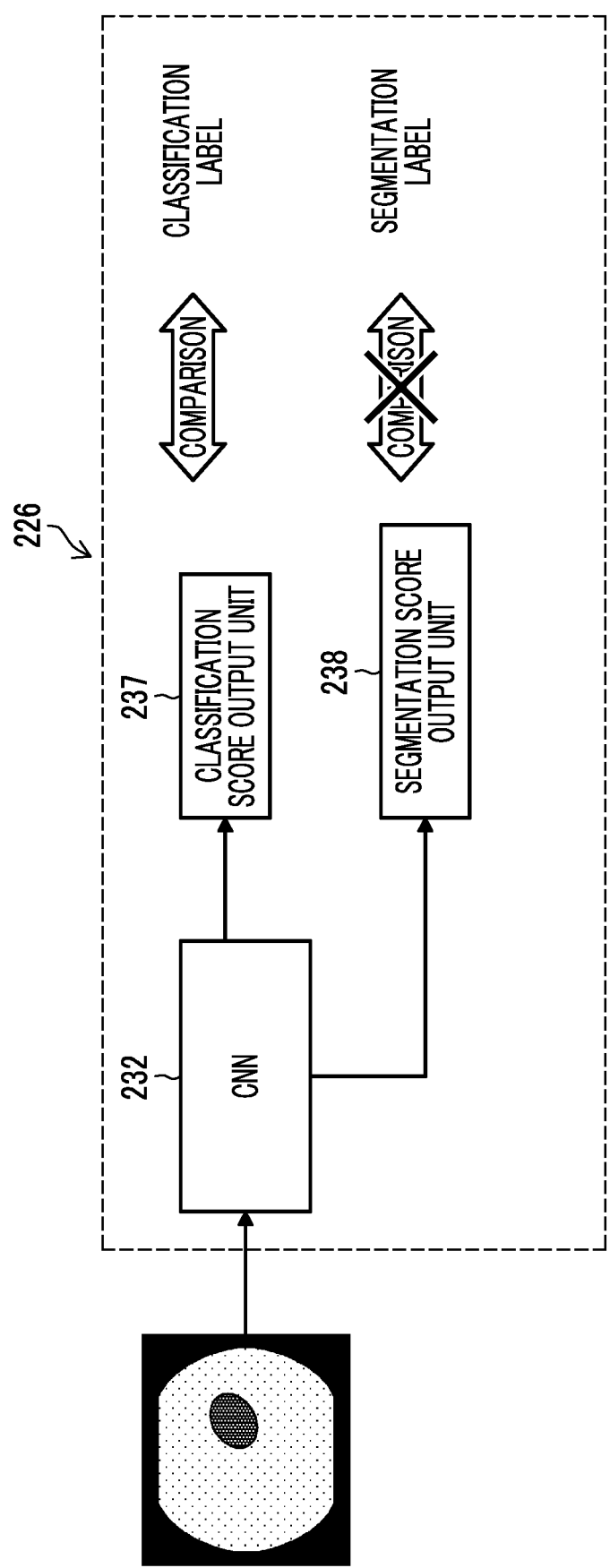
FIG. 13 is a flowchart illustrating update processing of a weight coefficient according to presence or absence of region information acquisition.

Update of Weight Coefficient According to Presence or Absence of Region Information In the above-described first embodiment, the region information (mask image of the recognition target) is acquired for each image (image including the recognition target) of the first image group, but CNN learning generally requires a large amount of learning data, and thus preparing mask images for all of the data requires a considerable cost. Thus, in the modification example, instead of acquiring the region information for all of the images for learning, the region information is acquired for a certain number of images in the learning data. Then, for the data without the mask image, the recognition unit 226 controls such that the segmentation learning part does not affect the update of the weight coefficient during learning (for example, the segmentation score is not compared with the segmentation label; refer to FIG. 13).

Figure 14:
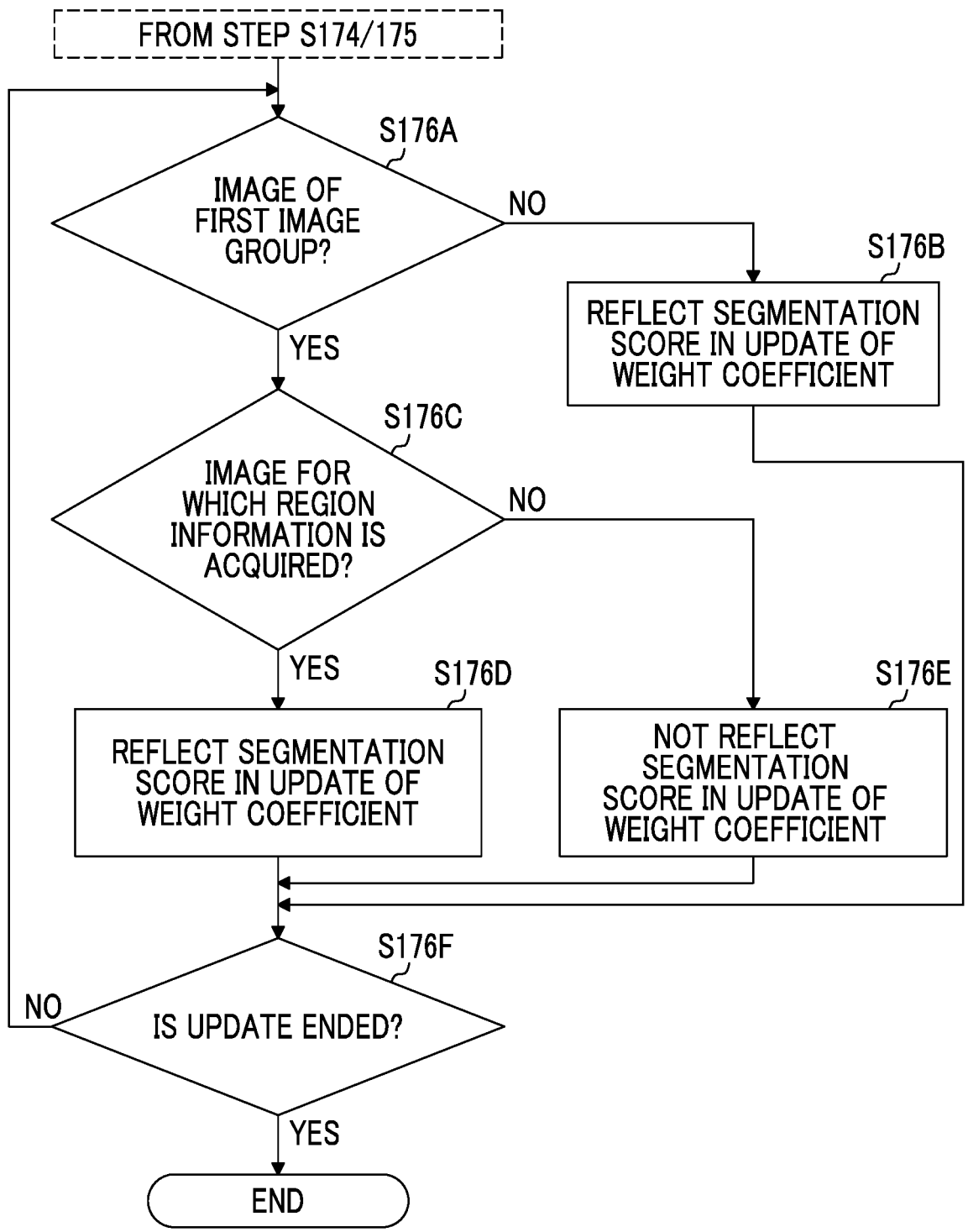
FIG. 14 is a diagram illustrating a state of learning in a case of an image including a recognition target but no segmentation label.

Specifically, in the update processing of the weight coefficient (refer to Step S176 of FIG. 12), as illustrated in the flowchart of FIG. 14, the recognition unit 226 determines whether the update of the weight coefficient is for the image of the first image group (Step S176A: weight coefficient update step). In a case where the determination result is NO, that is, in a case where the update of the weight coefficient is for the image of the second image group, the processing proceeds to Step S176B, and the recognition unit 226 reflects the segmentation score in the update of the weight coefficient (weight coefficient update step).

On the other hand, in a case where the determination result of Step S176A is YES, that is, in a case where the update of the weight coefficient is for the image of the first image group, the processing proceeds to Step S176C, and the recognition unit 226 determines whether the update of the weight coefficient is for the image for which the region information is acquired (weight coefficient update step). In a case where the determination result of Step S176C is YES, the processing proceeds to Step S176D, and the recognition unit 226 reflects the segmentation score in the update of the weight coefficient (weight coefficient update step). In a case where the determination result of Step S176C is NO, the processing proceeds to Step S176E, and the recognition unit 226 does not reflect the segmentation score in the update of the weight coefficient (weight coefficient update step). The recognition unit 226 repeats the processing of Steps S176A to S176E until the update of the weight coefficient is ended for all of the images (until YES in Step S176F).

According to the modification example, since the region information (mask image of the recognition target) is acquired only for a certain number of images in the learning data (images of the first image group), it is possible to reduce the cost of creating mask images. The number of images for which the region information is acquired can be determined in consideration of the learning accuracy, the cost of creating the mask images, and the like.

Modification Example of Configuration of Recognition Unit

Figure 15:
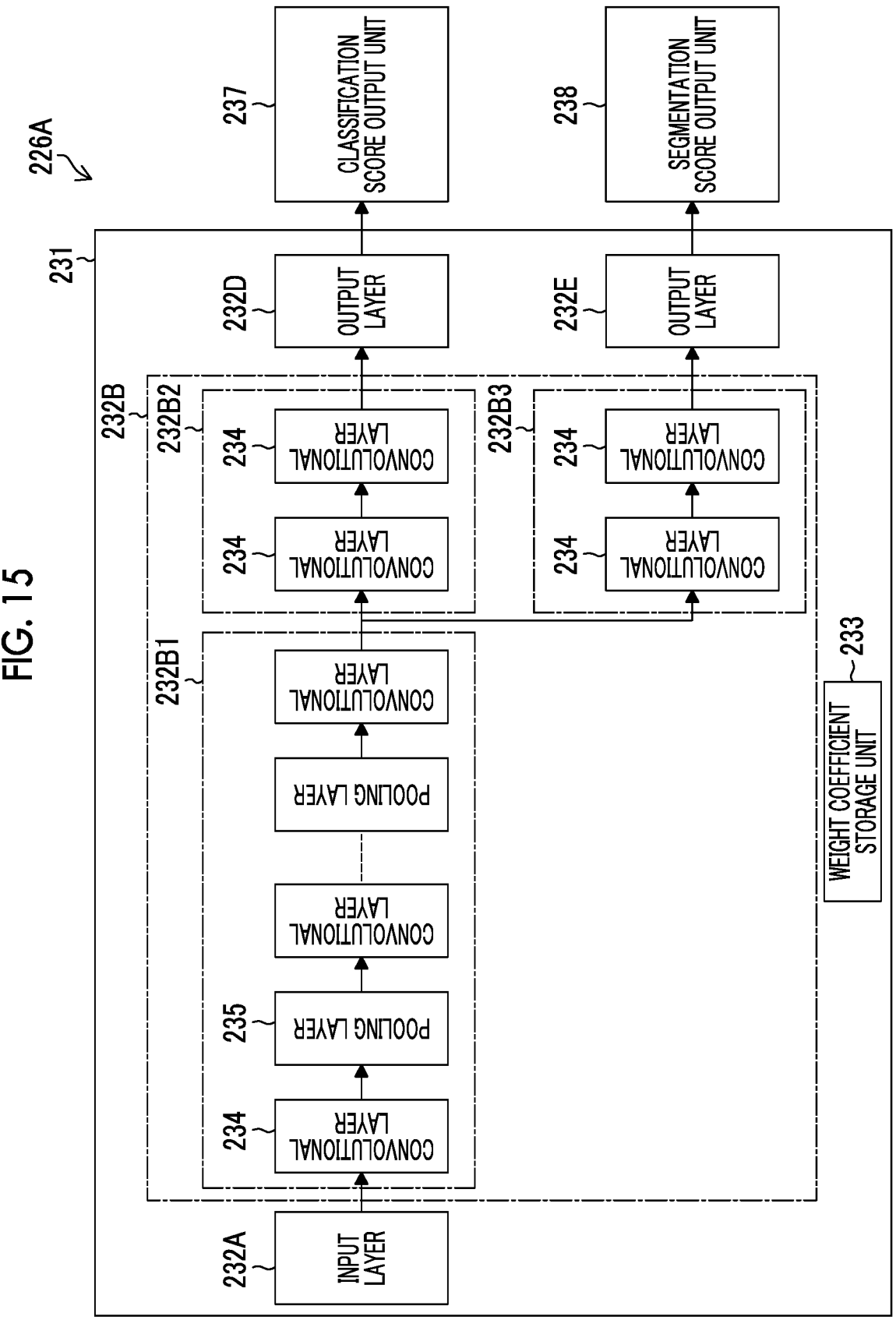
FIG. 15 is a diagram illustrating a modification example of the configuration of the recognition unit.

FIG. 15 is a diagram illustrating a modification example of the configuration of the recognition unit. In a recognition unit 226A illustrated in FIG. 15, the intermediate layer 232B of a CNN 231 branches off in the middle to have three intermediate layer groups (intermediate layer 232B1, intermediate layer 232B2, intermediate layer 232B3). The intermediate layer 232B1 refers to a third weight coefficient group (third weight coefficient group), the intermediate layer 232B2 refers to a first weight coefficient group (first weight coefficient group), and the intermediate layer 232B3 refers to a second weight coefficient group (second weight coefficient group). The first weight coefficient group is a weight coefficient group referred to only in a case where the first task (classification) is performed to output the classification score as the evaluation result, the second weight coefficient group is a weight coefficient group referred to only in a case where the second task (segmentation) is performed to output the evaluation result, and the third weight coefficient group is a weight coefficient group referred to in a case where any of the first task and the second task is performed. The weight coefficient storage unit 233 stores the first to third weight coefficient groups as the weight coefficient.

The intermediate layers 232B1 to 232B3 include the convolutional layer 234 and the pooling layer 235. In addition, the intermediate layers 232B1 to 232B3 may include a layers that performs batch normalization and a fully connected layer. The output of the output layer 232D is input to the classification score output unit 237, and the output of the output layer 232E is input to the segmentation score output unit 238.

Learned Neural Network and Medical Image Classification Device

By using the CNN 232 (learned neural network, learned model) learned by the medical image learning method (image learning method) according to the first embodiment, the medical image classification device can be configured which performs classification processing on time-series endoscopic images acquired via the endoscope scope 100 (in which the classification score output unit 237 outputs the classification score). In the medical image classification device, the input image is classified into any of the predetermined classes, as the first task (classification), for example. Then, since the determination on "whether the object is included" can be made by referring to the result of the second task (segmentation), it is possible to perform control such as not displaying the classification result in a case where the object is not included.

As described above, according to the endoscope system 10 (endoscope device, image learning device, medical image learning device), the image learning method (medical image learning method), the neural network, and the image classification device according to the first embodiment, it is possible to determine that the object is not included by learning the images which do not include the object by the second task. For the images which do not include the recognition target, it is possible to prevent an incorrect result from being output and to support proper classification of images.

Second Embodiment

A second embodiment will be described focusing on the differences from the first embodiment. The same reference numerals are given to the same configurations as those of the first embodiment, and the detailed description thereof will be omitted.

Figure 16:
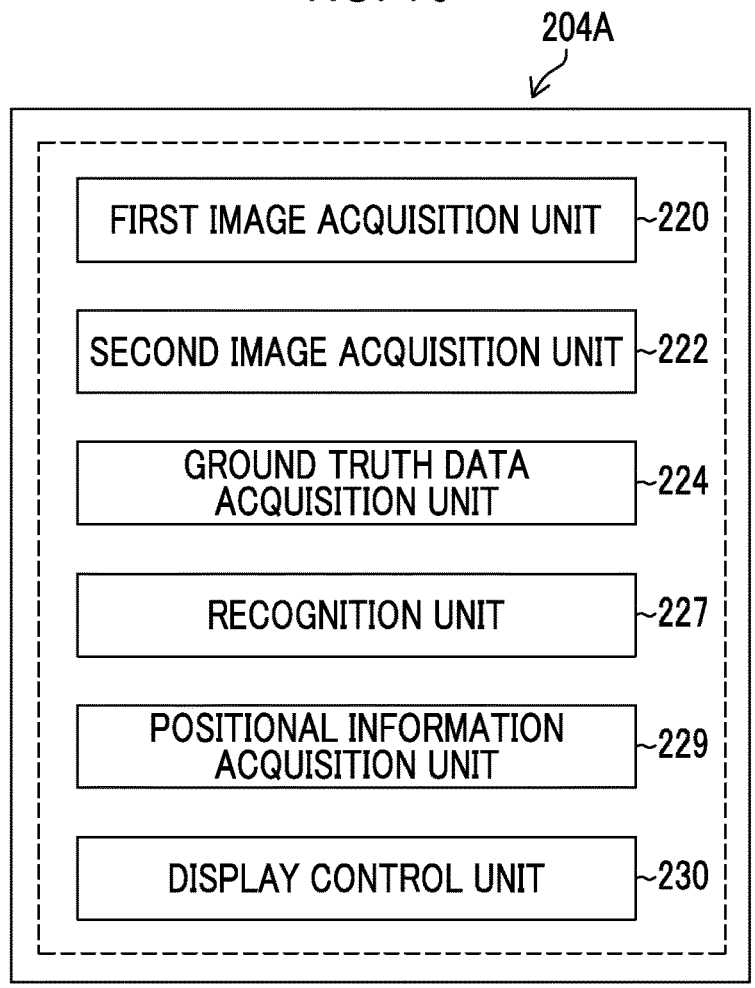
FIG. 16 is a diagram illustrating a functional configuration of an image processing unit according to a second embodiment.

FIG. 16 is a functional block diagram of an image processing unit 204A according to the second embodiment. The image processing unit 204A is different from the image processing unit 204 (refer to FIG. 3) according to the first embodiment in that the image processing unit 204A has a recognition unit 227 and a positional information acquisition unit 229 (positional information acquisition unit) and the ground truth data acquisition unit 224 (ground truth data acquisition unit, ground truth position label generation unit) functions as a ground truth position label generation unit.

Figure 17:
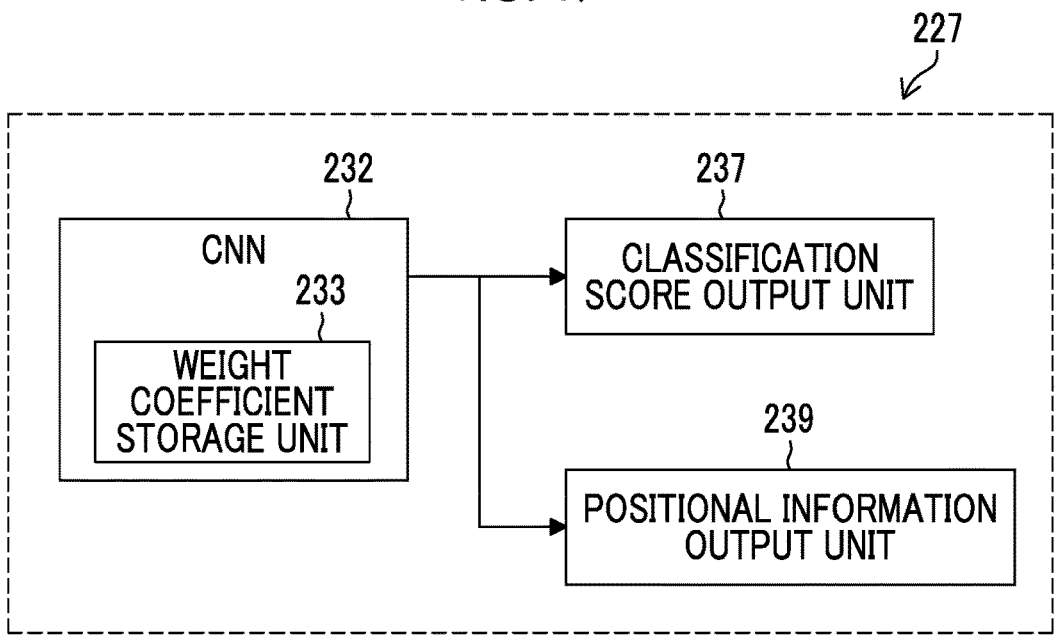
FIG. 17 is a diagram illustrating a configuration of a recognition unit according to the second embodiment.

FIG. 17 is a diagram illustrating a configuration of the recognition unit 227. The recognition unit 227 has a positional information output unit 239 (estimated positional information output unit) that estimates the positional information of the recognition target as the second task and outputs estimated positional information as the evaluation result. In this manner, in the second embodiment, the CNN 232 is provided with the classification score output unit 237 and the positional information output unit 239, and classification and positional information estimation are learned with the same neural network (refer to FIG. 17). The other configurations of the endoscope system are the same as those of the first embodiment.

Figure 18:
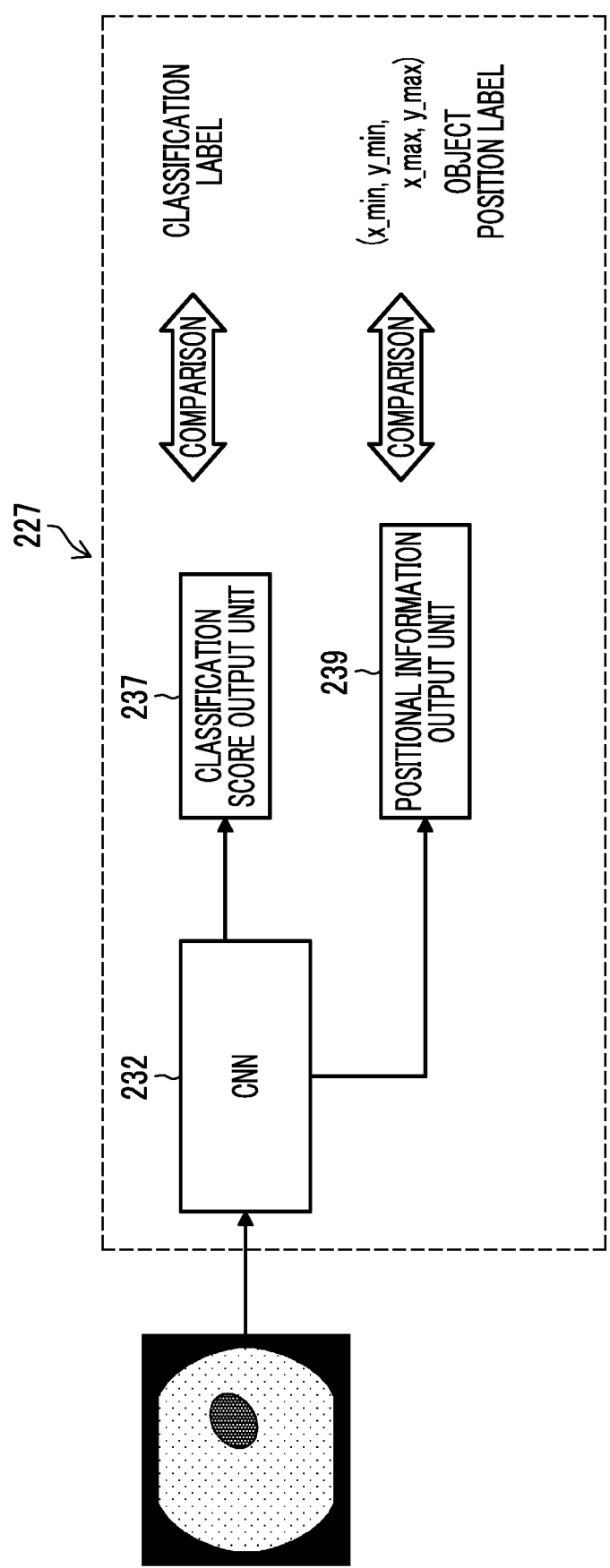
FIG. 18 is a diagram illustrating a state of learning in a case where an image includes a recognition target.
Figure 19:
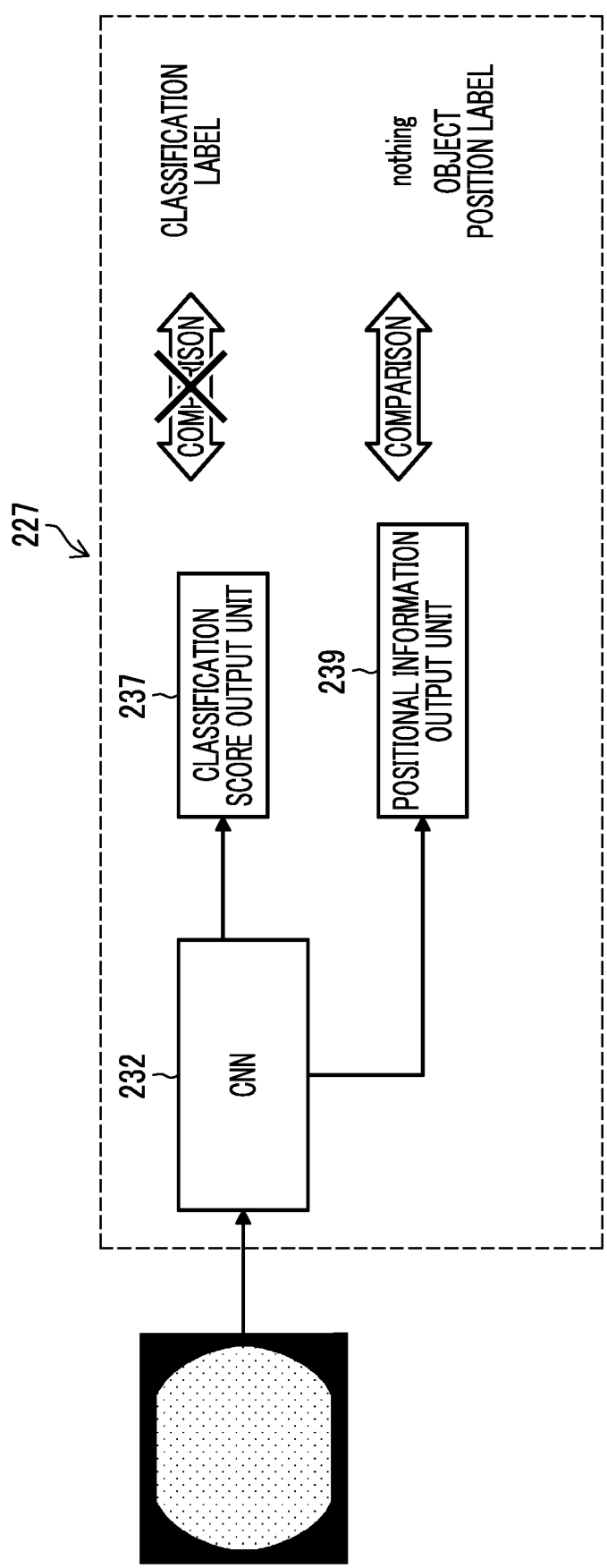
FIG. 19 is a diagram illustrating a state of learning in a case where an image does not include a recognition target.

FIG. 18 is a diagram illustrating a state of learning in a case where the recognition target is included, and FIG. 19 is a diagram illustrating a state of learning in a case where the recognition target is not included. In a case where the recognition target is included, learning is performed to detect the recognition target in the image (to estimate the positional information), and in a case where the recognition target is not included, learning is performed so as to detect nothing (not to estimate the positional information). By performing learning in this manner, in the inference processing of detection, the estimated positional information of the recognition target is output for the image including the recognition target, and the positional information is not output in a case where the recognition target is not included. Therefore, it is possible to determine the image which does not include the recognition target. As described above for the first embodiment, the classification score output for the image (image of the second image group) which does not include the recognition target is not reflected in the update of the weight coefficient.

Figure 20:
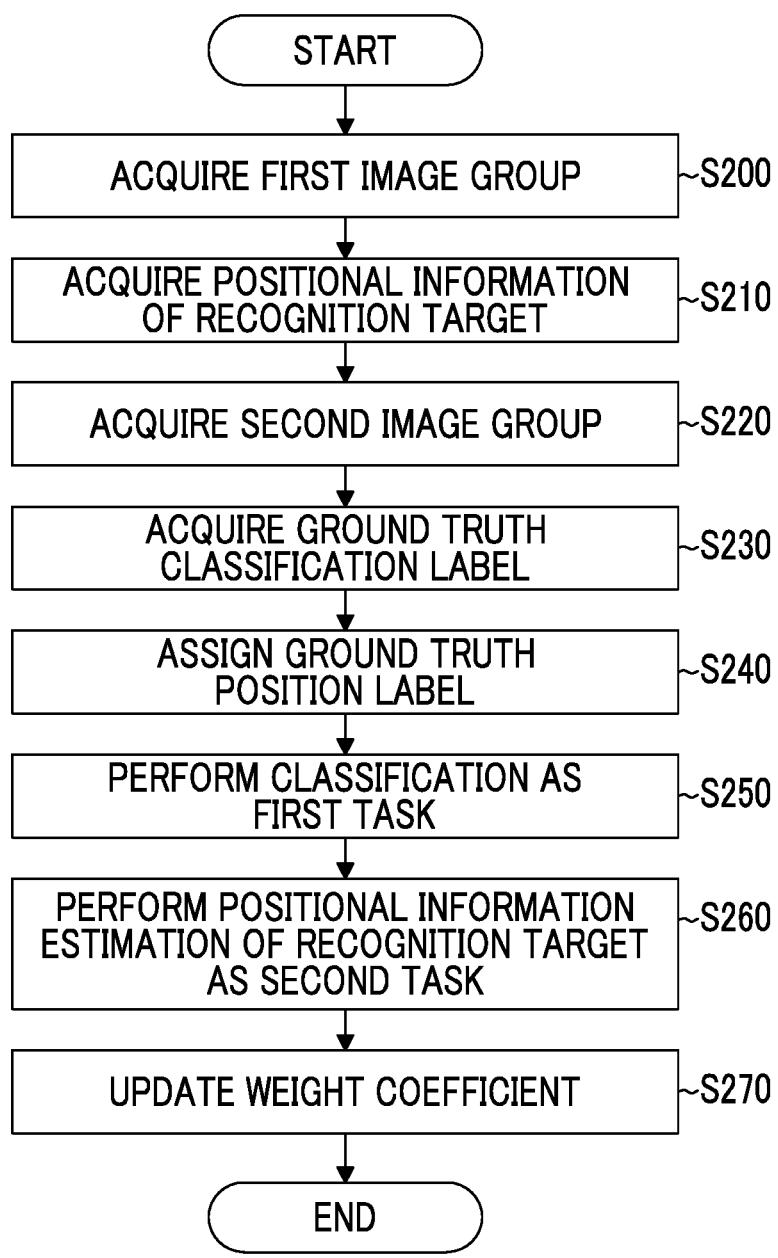
FIG. 20 is a flowchart illustrating processing of an image learning method according to the second embodiment.

FIG. 20 is a flowchart illustrating processing of an image learning method according to the second embodiment. Since processing of Steps S200, S220, S230, and S250 is the same as the processing of Steps S100, S120, S130, and S150 described above (refer to FIG. 10), the detailed description thereof will be omitted.

The positional information acquisition unit 229 acquires the positional information of the recognition target in the image, for at least one image of the first image group (image group composed of images each including at least one recognition target) (Step S210: positional information acquisition step). For example, the "positional information" may be a mask image of the classification target or a marking image in which the classification target is surrounded by the free curve, or may be coordinate information itself. The recognition unit 227 generates the ground truth position label associated with the image as the "ground truth data" for the image, for which the positional information is acquired, among the images of the first image group and the images of the second image group (image group composed of images not including the recognition target), on the basis of the positional information acquired in Step S210 (Step S240: ground truth position label generation step) as will be described below. The recognition unit 227 can generate coordinates indicating four vertices of a rectangle (bounding box) surrounding, for example, the recognition target, as the "ground truth position label".

The recognition unit 227 estimates the positional information of the recognition target on the basis of the image input by the input unit and the weight coefficient in Step S260 (positional information estimation step), and the positional information output unit 239 outputs the estimated positional information as the evaluation result (second task).

The recognition unit 227 (neural network) updates the weight coefficient on the basis of the results of the first task (classification) and the second task (positional information estimation) (Step S270: weight coefficient update step). The update of the weight coefficient for the first task is the same as in the first embodiment (Step S170), and the recognition unit 227 updates the weight coefficient for the second task (positional information estimation) on the basis of the comparison result between the estimated positional information output by inputting the image of the first image group and the image of the second image group and the ground truth position label associated with the input image.

Figure 21:
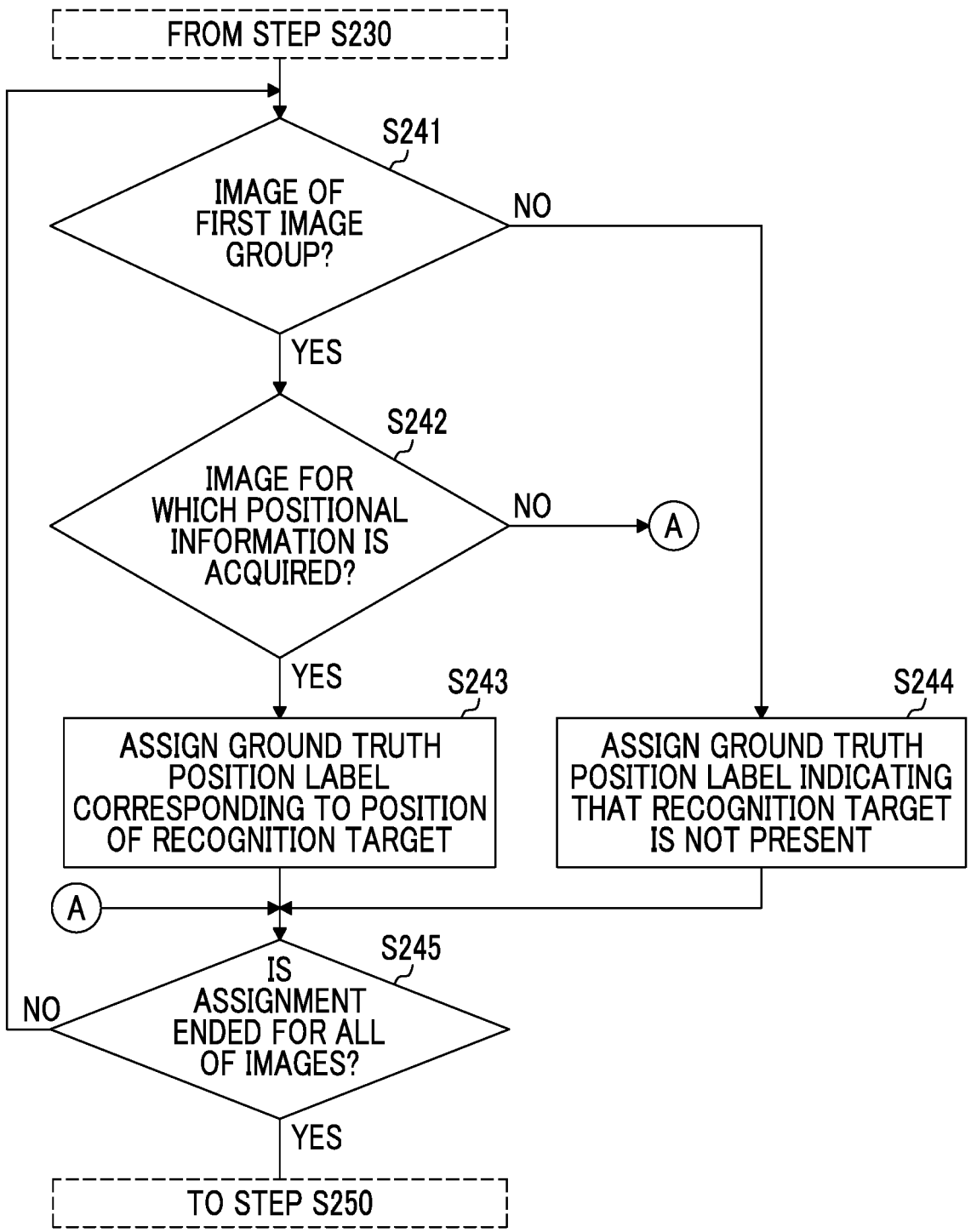
FIG. 21 is a flowchart illustrating generation processing of a ground truth position label.

FIG. 21 is a flowchart illustrating details of processing of assigning the ground truth position label. The recognition unit 227 determines whether the processing target image is the image of the first image group (Step S241). In a case where the processing target image is the image of the first image group, the processing proceeds to Step S242. In a case where the processing target image is not the image of the first image group (in a case where the processing target image is the image of the second image group), the processing proceeds to Step S244, and the ground truth position label indicating that the recognition target is not present is assigned. In Step S242, the recognition unit 227 determines whether the processing target image is the image for which the positional information is acquired in Step S210. In a case where the processing target image is the image for which the positional information is acquired, the processing proceeds to Step S243, and the ground truth position label corresponding to the position of the recognition target is assigned. In a case where the processing target image is not the image for which the positional information is acquired, the processing proceeds to Step S245 without assigning the ground truth position label. The recognition unit 227 repeats the processing of Steps S241 to S244 until the assignment of the ground truth position label is ended for all of the images (until YES in Step S245).

Modification Example of Update of Weight Coefficient

Figure 22:
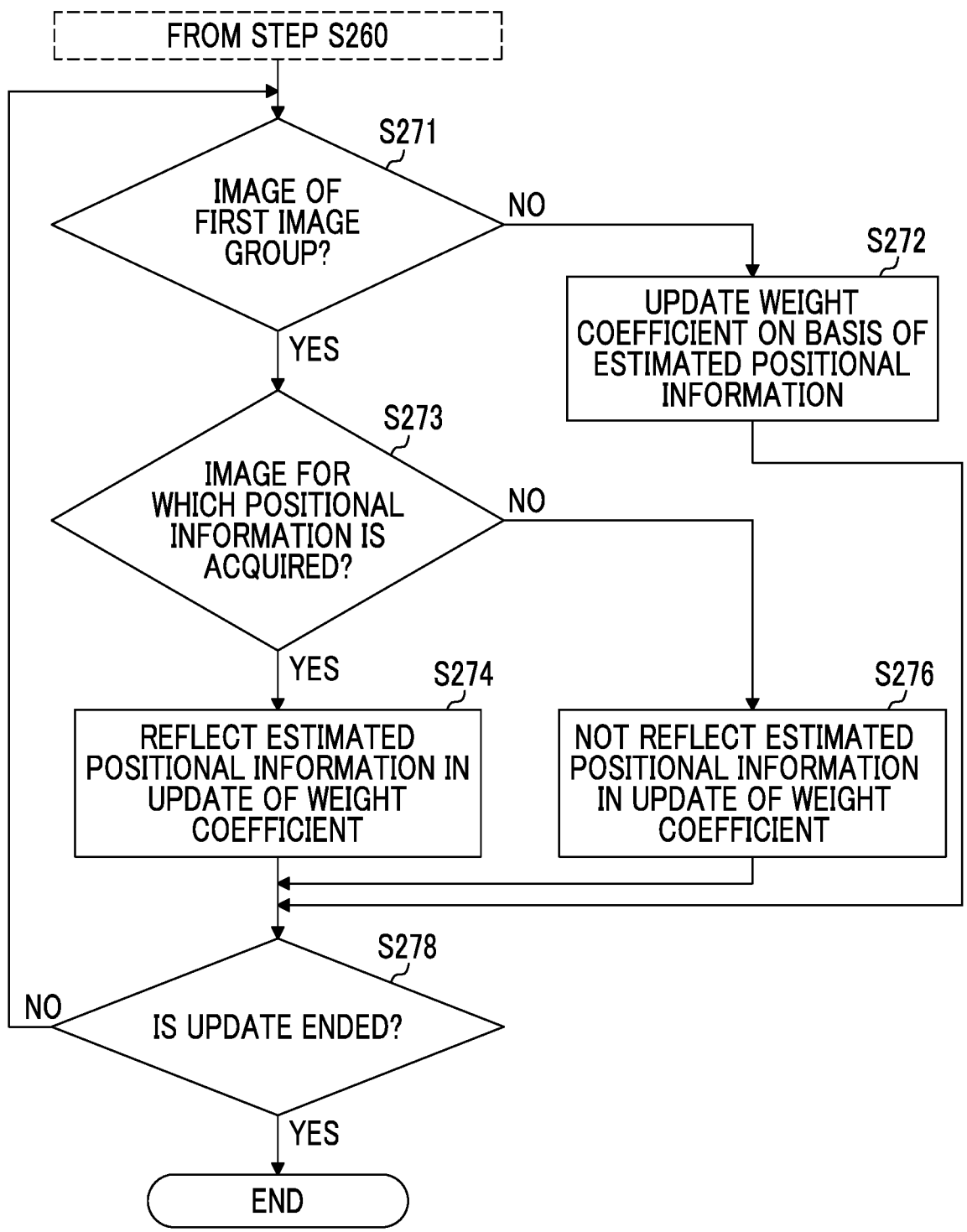
FIG. 22 is a flowchart illustrating update processing of a weight coefficient according to presence or absence of positional information acquisition.

FIG. 22 is a flowchart illustrating a modification example of the update of the weight coefficient in the second embodiment. In the modification example, the recognition unit 227 determines whether the update of the weight coefficient is for the image of the first image group (Step S271: weight coefficient update step). In a case where the determination result is NO, that is, in a case where the update of the weight coefficient is for the image of the second image group, the processing proceeds to Step S272, and the weight coefficient is updated on the basis of the comparison result between the estimated positional information and the ground truth position label associated with the image. In a case where the determination result in Step S271 is YES, that is, in a case where the update of the weight coefficient is for the image of the first image group, the processing proceeds to Step S273, and the recognition unit 227 determines whether the update of the weight coefficient is for the image for which the positional information is acquired (weight coefficient update step). In a case where the determination result is YES, the processing proceeds to Step S274, and the estimated positional information is reflected in the update of the weight coefficient (weight coefficient update step). Specifically, the recognition unit 227 updates the weight coefficient on the basis of the comparison result between the estimated positional information output by inputting the image of the first image group and the ground truth position label associated with the input image. On the other hand, for the image, for which the positional information acquisition unit does not acquire the positional information, among the images of the first image group, the recognition unit 227 does not reflect the estimated positional information output for the corresponding image in the update of the weight coefficient (Step S276: weight coefficient update step). The recognition unit 227 repeats the processing of Steps S272 to S276 until the update of the weight coefficient is ended for all of the images. The update of the weight coefficient may be any of batch processing, mini-batch processing, and sequential processing as in the first embodiment.

OTHER MODIFICATION EXAMPLES

Also in the second embodiment, the same modification example as that of the first embodiment can be adopted in addition to the above-described modification example. For example, as in the example of FIG. 15, the intermediate layer of the CNN 232 can be made to branch off in the middle so as to be provided with three intermediate layer groups, and first to third weight coefficient groups can be stored to correspond to the respective intermediate layer groups. In this case, the recording unit 207 records the first weight coefficient group referred to only in a case where the first task (classification) is performed, the second weight coefficient group referred to only in a case where the second task (positional information estimation) is performed, and the third weight coefficient group referred to in a case where any of the first task and the second task is performed.

The learned neural network (learned model) can be obtained by the image learning method according to the second embodiment, and the image classification device (medical image classification device) can be configured by performing classification processing of the image using the learned neural network.

As described above, even in the endoscope system (endoscope device, image learning device, medical image learning device), the image learning method (medical image learning method), the neural network, and the image classification device according to the second embodiment, it is possible to prevent an incorrect result from being output for the image which does not include the recognition target and to support proper classification of images.

Application to Medical Image Other than Endoscopic Image

The case of performing recognition using the endoscopic image as one aspect of the medical image (image for medical use) has been described in the first and second embodiments and the modification examples, but the image learning device, the image learning method, the neural network, and the image classification method according to an embodiment of the invention can be applied to the case of using a medical image other than the endoscopic image such as an ultrasound image diagnostic apparatus.

Application to Image Other than Medical Image

The case of using the medical image has been described in the first and second embodiments and the modification examples, but the image learning device, the image learning method, the neural network, and the image classification device according to an embodiment of the invention can be applied to a case of handling an image other than the medical image. For example, in video recognition such as automatic driving, while a task (first task) of classifying an object (recognition target) such as people and cars is learned, a background image that does not include the object can be learned in the second task. Further, in a case of classifying objects from images on the factory line (classifying quality of products and the like), while a task (first task) of classifying objects is learned, background images that do not include the objects can be learned in the second task.

Additional Remarks

Configurations to be described below are also included in the scope of the invention in addition to the first and second embodiments and other application examples described above.

Additional Remark 1

A medical image processing device comprising: a medical image analysis processing unit that detects a region of interest, which is a region to be noticed, on the basis of a feature quantity of pixels of a medical image; and a medical image analysis result acquisition unit that acquires an analysis result of the medical image analysis processing unit.

Additional Remark 2

The medical image processing device comprising: a medical image analysis processing unit that detects presence or absence of an object to be noticed, on the basis of a feature quantity of pixels of a medical image; and a medical image analysis result acquisition unit that acquires an analysis result of the medical image analysis processing unit.

Additional Remark 3

The medical image processing device, wherein the medical image analysis result acquisition unit acquires the analysis result of the medical image from a recording device, and the analysis result includes any one or both of the region of interest that is the region to be noticed included in the medical image and presence or absence of the object to be noticed.

Additional Remark 4

The medical image processing device, wherein the medical image is a normal light image that is obtained from the application of light in a white-light wavelength range or light in a plurality of wavelength ranges as the light in a white-light wavelength range.

Additional Remark 5

The medical image processing device, wherein the medical image is an image that is obtained from the application of light in a specific wavelength range, and the specific wavelength range is a range narrower than the white-light wavelength range.

Additional Remark 6

The medical image processing device, wherein the specific wavelength range is a blue-light wavelength range or a green-light wavelength range of a visible-light wavelength range.

Additional Remark 7

The medical image processing device, wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

Additional Remark 8

The medical image processing device, wherein the specific wavelength range is a red-light wavelength range of a visible-light wavelength range.

Additional Remark 9

The medical image processing device, wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

Additional Remark 10

The medical image processing device, wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

Additional Remark 11

The medical image processing device, wherein the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

Additional Remark 12

The medical image processing device, wherein the medical image is an in-vivo image of the inside of a living body, and the in-vivo image has information of fluorescence emitted by fluorescent materials in the living body.

Additional Remark 13

The medical image processing device, wherein the fluorescence is obtained from the application of excitation light, which has a peak wavelength in a wavelength range of 390 nm to 470 nm, to the inside of the living body.

Additional Remark 14

The medical image processing device, wherein the medical image is an in-vivo image of the inside of a living body, and the specific wavelength range is an infrared wavelength range.

Additional Remark 15

The medical image processing device, wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

Additional Remark 16

The medical image processing device, wherein a medical image acquisition unit comprises a special light image acquisition unit that acquires a special light image having information about the specific wavelength range on the basis of a normal light image obtained from the application of light in a white-light wavelength range or light in a plurality of wavelength ranges as the light in a white-light wavelength range, and the medical image is the special light image.

Additional Remark 17

The medical image processing device, wherein a signal in the specific wavelength range is obtained from an arithmetic operation based on color information about RGB or CMY included in the normal light image.

Additional Remark 18

The medical image processing device further comprising: a feature quantity image generation unit generating a feature quantity image from an arithmetic operation based on at least one of the normal light image that is obtained from the application of light in a white-light wavelength range or light in a plurality of wavelength ranges as the light in a white-light wavelength range and the special light image that is obtained from the application of light in a specific wavelength range, wherein the medical image is the feature quantity image.

Additional Remark 19

An endoscope device comprising: the medical image processing device according to any one of Additional remarks 1 to 18; and an endoscope that acquires an image from the application of at least one of light in a white-light wavelength range or light in the specific wavelength range.

Additional Remark 20

A diagnosis support apparatus comprising: the medical image processing device according to any one of Additional remarks 1 to 18.

Additional Remark 21

A medical service support apparatus comprising: the medical image processing device according to any one of Additional remarks 1 to 18.

The embodiment and other examples of the invention have been described above, but the invention is not limited to the above-described aspects and can have various modifications without departing from the scope of the invention.

EXPLANATION OF REFERENCES

10: endoscope system
100: endoscope scope
102: hand operation part
104: insertion part
106: universal cable
108: light guide connector
112: soft portion
114: bendable portion
116: hard distal end portion
116A: distal end-side end face
123: illumination unit
123A: illumination lens
123B: illumination lens
126: forceps port
130: imaging optical system
132: imaging lens
134: imaging element
136: drive circuit
138: AFE
141: air/water supply button
142: suction button
143: function button
144: imaging button
170: light guide
200: processor
202: image input controller
204: image processing unit
204A: image processing unit
205: communication control unit
206: video output unit 207: recording unit
208: operation unit
209: voice processing unit
209A: speaker
210: CPU
211: ROM
212: RAM
220: first image acquisition unit
222: second image acquisition unit
224: ground truth data acquisition unit
226: recognition unit
226A: recognition unit
227: recognition unit
228: region information acquisition unit
229: positional information acquisition unit
230: display control unit
231: CNN
232: CNN
232A: input layer
232B: intermediate layer
232B1: intermediate layer
232B2: intermediate layer
232B3: intermediate layer
232C: output layer
232D: output layer
232E: output layer
233: weight coefficient storage unit
234: convolutional layer
235: pooling layer
236: fully connected layer
237: classification score output unit
238: segmentation score output unit
239: positional information output unit
260: first image group
262: second image group
264: ground truth data
300: light source device
310: light source
310B: blue light source
310G: green light source
310R: red light source
310V: violet light source
330: stop
340: condenser lens
350: light source control unit
400: monitor
F1: filter
F2: filter
Fn: filter
S100 to S278: each step of image learning method

What is claimed is:

1. An image learning device comprising:
a first image acquisition unit that acquires a first image group composed of images each including at least one recognition target;
a second image acquisition unit that acquires a second image group composed of images not including the recognition target;
a ground truth data acquisition unit that acquires ground truth data associated with the images; and
a neural network that includes an input unit that inputs an image, a weight coefficient storage unit that stores a weight coefficient to be applied to the input image, and an output unit that outputs an evaluation result of the input image on the basis of the input image and the weight coefficient, and performs a first task of classifying the recognition target in the input image and outputting a classification score as the evaluation result, and a second task which is different from the first task and is performed on the input image,
wherein the ground truth data acquisition unit
acquires a ground truth classification label associated with the image of the first image group as the ground truth data, for the first task, and
acquires the ground truth data associated with the image of the first image group and the ground truth data associated with the image of the second image group, for the second task, and
the neural network
for the first task, updates the weight coefficient on the basis of a comparison result between the classification score output for the image of the first image group and the ground truth classification label, and does not reflect the classification score output for the image of the second image group in an update of the weight coefficient, and
for the second task, updates the weight coefficient on the basis of the evaluation result output for the image of the first image group and the evaluation result output for the image of the second image group.

2. The image learning device according to claim 1, further comprising:
a region information acquisition unit that acquires region information of the recognition target in the image, for at least one image of the first image group,
wherein the ground truth data acquisition unit further includes a segmentation label generation unit that
generates, as the ground truth data, a ground truth segmentation label associated with the image, for the image, for which the region information is acquired, among the images of the first image group and the image of the second image group,
assigns a predetermined class as the ground truth segmentation label, for all of small regions of the image of the second image group and a small region not corresponding to the recognition target among small regions of the image of the first image group, and
assigns a class label different from the predetermined class, as the ground truth segmentation label, for a small region corresponding to the recognition target among the small regions of the image of the first image group, and
the neural network has a segmentation score output unit that performs segmentation as the second task on the basis of the image input by the input unit and the weight coefficient, and outputs a segmentation score as the evaluation result for each small region of the image, and
the neural network updates the weight coefficient on the basis of a comparison result between the segmentation score output by inputting the image of the first image group and the image of the second image group and the ground truth segmentation label associated with the input image.

3. The image learning device according to claim 2,
wherein the neural network does not reflect the segmentation score output for the image, for which the region information is not acquired, among the images of the first image group in the update of the weight coefficient.

4. The image learning device according to claim 2,
wherein the ground truth segmentation label has a lower resolution than a resolution of the input image.

5. The image learning device according to claim 1, further comprising:
- a positional information acquisition unit that acquires positional information of the recognition target in the image, for at least one image of the first image group, wherein the ground truth data acquisition unit further includes a ground truth position label generation unit that
- generates, as the ground truth data, a ground truth position label associated with the image, for the image, for which the positional information is acquired, among the images of the first image group and the image of the second image group,
- assigns a ground truth position label indicating that the recognition target is not present to the image of the second image group, and
- assigns a ground truth position label corresponding to a position of the recognition target to the image of the first image group, the neural network has an estimated positional information output unit that estimates positional information of the recognition target as the second task and outputs estimated positional information as the evaluation result on the basis of the image input by the input unit and the weight coefficient, and the neural network updates the weight coefficient on the basis of a comparison result between the estimated positional information output by inputting the image of the first image group and the image of the second image group and the ground truth position label associated with the input image.

6. The image learning device according to claim 5, wherein the neural network does not reflect the estimated positional information output for the image, for which the positional information acquisition unit does not acquire the positional information, among the images of the first image group, in the update of the weight coefficient.

7. The image learning device according to claim 1, wherein the weight coefficient storage unit stores as the weight coefficient
- a first weight coefficient group referred to only in a case where the first task is performed to output the classification score as the evaluation result,
- a second weight coefficient group referred to only in a case where the second task is performed to output the evaluation result, and
- a third weight coefficient group referred to in a case where any of the first task and the second task is performed.

8. The image learning device according to claim 1, wherein the image of the first image group and the image of the second image group are images captured by the same kind of imaging device.

9. The image learning device according to claim 1, wherein the recognition target is a histological structure of a target to be imaged.

10. The image learning device according to claim 1, wherein the image of the first image group and the image of the second image group are images acquired by an endoscope device.

11. An image learning method using a neural network including an input unit that inputs an image, a weight coefficient storage unit that stores a weight coefficient to be applied to the input image, and an output unit that outputs an evaluation result of the input image on the basis of the input image and the weight coefficient, the image learning method comprising:
- acquiring a first image group composed of images each including at least one recognition target;
- acquiring a second image group composed of images not including the recognition target;
- acquiring ground truth data associated with the images;
- executing a first task of classifying the recognition target in the input image and outputting a classification score as the evaluation result;
- executing a second task different from the first task on the input image; and
- updating the weight coefficient on the basis of results of the first task and the second task, wherein in the acquiring of the ground truth data,
- a ground truth classification label associated with the image of the first image group is acquired as the ground truth data, for the executing of the first task, and
- the ground truth data associated with the image of the first image group and the ground truth data associated with the image of the second image group are acquired for the executing of the second task, and in the updating of the weight coefficient,
- the weight coefficient is updated on the basis of a comparison result between the classification score output for the image of the first image group and the ground truth classification label, and the classification score output for the image of the second image group is not reflected in an update of the weight coefficient, and
- the weight coefficient is updated on the basis of the evaluation result output for the image of the first image group and the evaluation result output for the image of the second image group.

12. A neural network learned by the image learning method according to claim 11.

13. An image classification device comprising:
- an image acquisition unit that acquires time-series images; and
- the neural network according to claim 12, wherein the image classification device performs classification processing on the acquired images using the neural network.

* * * * *